US009828628B2

(12) United States Patent
Vallé-Bélisle et al.

(10) Patent No.: US 9,828,628 B2
(45) Date of Patent: Nov. 28, 2017

(54) NUCLEOTIDE-BASED PROBES AND METHODS FOR THE DETECTION AND QUANTIFICATION OF MACROMOLECULES AND OTHER ANALYTES

(75) Inventors: Alexis Vallé-Bélisle, Goleta, CA (US); Francesco Ricci, Rome (IT); Ryan White, Santa Barbara, CA (US); Andrew J. Bonham, Santa Barbara, CA (US); Kevin W. Plaxco, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 541 days.

(21) Appl. No.: 13/988,487

(22) PCT Filed: Nov. 21, 2011

(86) PCT No.: PCT/US2011/061701
§ 371 (c)(1),
(2), (4) Date: Jul. 17, 2013

(87) PCT Pub. No.: WO2012/071344
PCT Pub. Date: May 31, 2012

(65) Prior Publication Data
US 2013/0288923 A1  Oct. 31, 2013

Related U.S. Application Data

(60) Provisional application No. 61/417,141, filed on Nov. 24, 2010.

(51) Int. Cl.
C12Q 1/68   (2006.01)
(52) U.S. Cl.
CPC ......... *C12Q 1/6825* (2013.01); *C12Q 1/6818* (2013.01)
(58) Field of Classification Search
None
See application file for complete search history.

(56) References Cited

U.S. PATENT DOCUMENTS

| | | | | |
|---|---|---|---|---|
| 5,925,517 A * | 7/1999 | Tyagi et al. | | 435/6.1 |
| 2004/0005595 A1* | 1/2004 | Browne | | C07H 21/04 506/9 |
| 2004/0219523 A1* | 11/2004 | Stanton | | C12Q 1/6825 435/6.14 |
| 2005/0106594 A1* | 5/2005 | Ellington | | C12N 15/111 435/6.11 |
| 2005/0118603 A1* | 6/2005 | Chun | | C12Q 1/6825 435/6.14 |
| 2005/0158720 A1* | 7/2005 | Li | | C12Q 1/6818 435/6.11 |
| 2007/0202498 A1 | 8/2007 | Aojula et al. | | |
| 2009/0104614 A1* | 4/2009 | Tsourkas | | C12Q 1/6818 435/6.11 |
| 2011/0151439 A1* | 6/2011 | Stratis-Cullum | .. | G01N 33/5308 435/6.1 |

FOREIGN PATENT DOCUMENTS

WO    2010/048002    4/2010

OTHER PUBLICATIONS

Hamaguchi et al. (Aptamer Beacons for the Direct Detection of Proteins, Anal Biochem. Jul. 15, 2001;294(2):126-31).*
Li et al. (Molecular Beacons: A Novel Approach to Detect Protein-DNA Interactions, Angew Chem Int Ed Engl. Mar. 2000;39(6):1049-1052).*
Narita et al. (Cis-regulatory hairpin-shaped mRNA encoding a reporter protein: catalytic sensing of nucleic acid sequence at single nucleotide resolution, Nat Protoc. 2007;2(5)1105-16).*
Santangelo et al. (Nanostructured Probes for RNA Detection in Living Cells, Ann Biomed Eng. Jan. 2006;34(1):39-50. Epub Feb. 7, 2006).*
Thurley et al. (Hairpin Peptide Beacon: Dual-Labeled PNA-Peptide-Hybrids for Protein Detection, J Am Chem Soc. Oct. 24, 2007;129(42):12693-5. Epub Oct. 10, 2007).*
Ihara et al. (Ferrocene—oligonucleotide conjugates for electrochemical probing of DNA, Nucleic Acids Res. Nov. 1, 1996; 24(21): 4273-4280).*
Lai et al. (Rapid, sequence-specific detection of unpurified PCR amplicons via a reusable, electrochemical sensor, Proc Natl Acad Sci U S A. Mar. 14, 2006; 103(11): 4017-4021. Published online Mar. 3, 2006).*
Wei et al. (Electrochemical detection of low-copy number salivary RNA based on specific signal amplification with a hairpin probe, Nucleic Acids Res. Jun. 2008; 36(11): e65. Published online May 17, 2008).*
Zhang et al. (Hairpin DNA Switch for Ultrasensitive Spectrophotometric Detection of DNA Hybridization Based on Gold Nanoparticles and Enzyme Signal Amplification, Anal Chem. Aug. 1, 2010;82(15):6440-6).*
Xu et al. (Electrochemical detection of sequence-specific DNA using a DNA probe labeled with aminoferrocene and chitosan modified electrode immobilized with ssDNA, Analyst. Jan. 2001;126(1):62-5).*
Broude et al. (Molecular Beacons and Other Hairpin Probes, in Encyclopedia of Diagnostic Genomics and Proteomics, pp. 846-850, Dec. 31, 2005).*
Borggrefe et al., "Quantitation of the RNA Polymerase II Transcription Machinery in Yeast," J Biol Chem 276:47150-47153 (2001).

* cited by examiner

*Primary Examiner* — Aaron Priest
(74) *Attorney, Agent, or Firm* — Rudy J. Ng; Carol L. Francis; Bozicevic, Field & Francis LLP

(57) ABSTRACT

Provided are unimolecular oligonucleotide probes for detecting a target in a sample. The probes use target binding-induced structural changes to detect the presence of the target in the sample. Also provided are methods of using the probes to detect a target in a sample.

23 Claims, 14 Drawing Sheets

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Probe
```

<400> SEQUENCE: 1 actttgttttt tttgcgttttt ttttcatagg                                          30

<210> SEQ ID NO 2
<211> LENGTH: 30
<212> TYPE: DNA
<213> ORGANISM: Artificial Sequence
<220> FEATURE:
<223> OTHER INFORMATION: Probe

<400> SEQUENCE: 2 actttgttttt ttttttttttt ttttcatagg                                          30

<210> SEQ ID NO 3
<211> LENGTH: 66
<212> TYPE: DNA
<213> ORGANISM: Artificial Sequence
<220> FEATURE:
<223> OTHER INFORMATION: Probe

<400> SEQUENCE: 3
tggatcggcg ttttattttc cttgttttttt tttttttttt ttcatggttt tattttgcgg          60
ctaggt                                                                      66

<210> SEQ ID NO 4
<211> LENGTH: 18
<212> TYPE: DNA
<213> ORGANISM: Artificial Sequence
<220> FEATURE:
<223> OTHER INFORMATION: Probe

<400> SEQUENCE: 4
taataaaacg ccgatcca                                                         18

<210> SEQ ID NO 5
<211> LENGTH: 18
<212> TYPE: PRT
<213> ORGANISM: Artificial Sequence
<220> FEATURE:
<223> OTHER INFORMATION: Probe

<400> SEQUENCE: 5

Glu Leu Leu Glu Leu Asp Lys Trp Ala Ser Leu Trp Asn Cys Ser Met
 1               5                  10                  15

Cys Cys

<210> SEQ ID NO 6
<211> LENGTH: 17
<212> TYPE: DNA
<213> ORGANISM: Artificial Sequence
<220> FEATURE:
<223> OTHER INFORMATION: Probe

<400> SEQUENCE: 6
aataaaacgc cgatcca                                                          17

<210> SEQ ID NO 7
<211> LENGTH: 68
<212> TYPE: DNA
<213> ORGANISM: Artificial Sequence
<220> FEATURE:
<223> OTHER INFORMATION: Probe

<400> SEQUENCE: 7

```
tggatcggcg ttttatttt ccttgttttt ttttttttt tttcatggtt tttattttgc    60
ggctaggt                                                            68

<210> SEQ ID NO 8
<211> LENGTH: 45
<212> TYPE: DNA
<213> ORGANISM: Artificial Sequence
<220> FEATURE:
<223> OTHER INFORMATION: Probe

<400> SEQUENCE: 8
gaataggttc ctataaaagg ttggttttat aaacctatcc tattc                   45
```

NUCLEOTIDE-BASED PROBES AND METHODS FOR THE DETECTION AND QUANTIFICATION OF MACROMOLECULES AND OTHER ANALYTES

CROSS-REFERENCE TO RELATED APPLICATIONS

This application claims the benefit of priority under 35 U.S.C. §119(e) to U.S. Provisional Patent Application No. 61/417,141, filed Nov. 24, 2010, the disclosure of which is hereby incorporated by reference in its entirety.

REFERENCE TO GOVERNMENT SUPPORT

This invention was made with government support under Grant Nos. R01EB007689 and 1R01AI076899 awarded by the National Institutes of Health. The government has certain rights in the invention.

INTRODUCTION

Existing bio-analytical assays, including ELISAs, western blots and PCR, are typically multistep, washing-intensive and reagent-intensive processes. As such, these approaches are not well suited for use outside the laboratory, or for real-time or in situ applications. In order to overcome this limitation, a number of sensors have been developed that detect binding in real time by monitoring a change in mass, charge or optical properties that occurs when the target binds a biomolecule-coated surface (e.g., surface plasmon resonance, field-effect transistor, quartz crystal microbalance and microcantilevers). However, these approaches detect adsorption to the sensor head rather than a specific binding per se, and thus cannot distinguish between the binding of the correct, authentic target and the non-specific binding of contaminants. Thus, these approaches are not suitable for detection of targets in complex samples, such as whole blood or blood serum.

SUMMARY

Provided are unimolecular oligonucleotide probes for the detection of a target in a sample. The probes use target binding-induced structural changes to detect the presence of the target in the sample. Also provided are methods of using the probes to detect a target in a sample.
Probes that Use Binding-Induced Segregation of Two Target Binding Moieties In some embodiments, the probes use target binding-induced structural changes to detect the presence of the target in the sample by utilizing binding-induced segregation of two target binding moieties as a signaling mechanism.

Accordingly, in some embodiments, a system for detecting one or more targets in a sample is provided. The system includes an oligonucleotide probe configured to produce a detectable signal when contacted by the one or more targets. The probe includes: (a) a first target binding moiety and a second target binding moiety; (b) a first hybridization sequence and a second hybridization sequence, where the first hybridization sequence and the second hybridization sequence are configured to form a duplex in the absence of the target binding to both the first target binding moiety and the second target binding moiety such that the first target binding moiety is positioned adjacent the second target binding moiety; and (c) a first signaling moiety and a second signaling moiety configured such that the position of the first signaling moiety is changed relative to the second signaling moiety upon binding of the one or more targets to both the first target binding moiety and the second target binding moiety. In addition, in the presence of the binding of the one or more targets to both the first target binding moiety and the second target binding moiety, formation of the duplex is inhibited such that the probe is configured to position the first signaling moiety relative to the second signaling moiety such that the probe produces a detectable change in a signal from the first and second signaling moieties.

Embodiments of the system may also include that the probe includes a stem-loop structure in the absence of the one or more targets binding to the first target binding moiety and the second target binding moiety.

Embodiments of the system may also include that the first target binding moiety and the second target binding moiety are bound directly to the probe.

Embodiments of the system may also include that the first target binding moiety and the second target binding moiety are bound indirectly to the probe.

Embodiments of the system may also include that the first target binding moiety and the second target binding moiety are bound to the probe through a linker moiety.

Embodiments of the system may also include that the probe further includes a third hybridization sequence and a fourth hybridization sequence. In these embodiments, the first target binding moiety may be bound to a fifth hybridization sequence complementary to the third hybridization sequence and the second target binding moiety may be bound to a sixth hybridization sequence complementary to the fourth hybridization sequence.

Embodiments of the system may also include that the third hybridization sequence and the fourth hybridization sequence are substantially the same, the fifth hybridization sequence and the sixth hybridization sequence are substantially the same. In these embodiments, the probe may include a frame inversion between the third hybridization sequence and the fourth hybridization sequence.

Embodiments of the system may also include that the frame inversion is a 3' to 3' or a 5' to 5' frame inversion.

Embodiments of the system may also include that the first target binding moiety and the second target binding moiety include antigens, and that the target includes an antibody specific for the antigens.

Embodiments of the system may also include that the first target binding moiety and the second target binding moiety include polypeptides that specifically bind to a macromolecule, and that the target includes the macromolecule.

Embodiments of the system may also include that the first target binding moiety and the second target binding moiety include aptamers that specifically bind to a macromolecule, and that the target includes the macromolecule.

Embodiments of the system may also include that the first target binding moiety and the second target binding moiety include DNA or RNA sequences that specifically bind to a macromolecule, and that the target includes the macromolecule.

Embodiments of the system may also include that the target has a concentration ranging from 10 pM to 300 pM.

Embodiments of the system may also include that the first signaling moiety includes a fluorophore and the second signaling moiety includes a quencher.

Embodiments of the system may also include that the first signaling moiety includes a first fluorophore and the second signaling moiety includes a second fluorophore.

Embodiments of the system may also include that the first signaling moiety includes a nanoparticle and the second signaling moiety includes a quencher.

Embodiments of the system may also include that the first signaling moiety includes a first nanoparticle and the second signaling moiety includes a second nanoparticle.

Embodiments of the system may also include that the first signaling moiety includes an electrochemical reporter and the second signaling moiety is an electrode.

Embodiments of the system may also include that the probe is immobilized on the surface of the electrode.

Embodiments of the system may also include that the first signaling moiety includes a macromolecule having a catalytic activity and the second signaling moiety includes an inhibitor or an activator of the catalytic activity.

Embodiments of the system may also include that the system includes an array of probes.

Aspects of the present disclosure also include a method of detecting a target in a sample. The method includes contacting a unimolecular oligonucleotide probe with the sample, whereby the target selectively binds to both the first target binding sequence and the second target binding sequence to form a target-probe hybrid. The method further includes detecting the presence or absence of the target-probe hybrid.

Embodiments of the method may also include that the sample includes a complex sample.

Embodiments of the method may also include that the sample includes whole blood.

Aspects of the present disclosure also include a method of detecting a second target in a sample. The method includes contacting an oligonucleotide probe with a first with the sample, whereby the target selectively binds to both the first target binding sequence and the second target binding sequence to form a target-probe hybrid. The method further includes contacting the target-probe hybrid with a second target, whereby the second target selectively binds the target and inhibits formation of the target-probe hybrid. The method further includes detecting the presence or absence of the target-probe hybrid.

Probes that Utilize Binding-Induced Reconstitution of a Recognition Element

In some embodiments, the probes use target binding-induced structural changes to detect the presence of the target in the sample by utilizing binding-induced reconstitution of a recognition element as a signaling mechanism. For example, the probe may use binding-induced reconstitution of a specific DNA binding sequence as signaling mechanism.

Aspects of the present disclosure include a system for detecting a DNA binding protein in a sample. The system includes a unimolecular oligonucleotide probe configured to produce a detectable signal when contacted with the DNA binding protein. The probe includes: (a) a first recognition sequence and a second recognition sequence, where the first and second recognition sequences are configured to form a recognition duplex specifically bound by the DNA binding protein in the sample; (b) a first hybridization sequence and a second hybridization sequence, where the first and second hybridization sequences are configured to form a second duplex in the absence of binding of the DNA binding protein to the recognition duplex; (c) a third hybridization sequence and a fourth hybridization sequence, where the third and fourth hybridization sequences are configured to form a third duplex in the absence of binding of the DNA binding protein to the recognition duplex; and (d) a first signaling moiety and a second signaling moiety, where in the absence of binding of the DNA binding protein to the recognition duplex, the first signaling moiety is positioned adjacent the second signaling moiety such that the probe does not produce a detectable signal. In addition, in the presence of binding of the DNA binding protein to the recognition duplex, formation of the second and third duplexes is inhibited such that the probe is configured to position the first signaling moiety away from the second signaling moiety such that the probe produces a detectable signal.

Embodiments of the system may also include that the first recognition sequence is positioned between the first and second hybridization sequences and the second recognition sequence is positioned between the third and fourth hybridization sequences.

Embodiments of the system may also include a fifth hybridization sequence and a sixth hybridization sequence, where fifth and sixth hybridization sequences are configured to form a fourth duplex in the absence of binding of the DNA binding protein to the recognition duplex.

Embodiments of the system may also include that at least a portion of the first recognition sequence is positioned between the second and third hybridization sequences and at least a portion of the second recognition sequence is positioned between the fourth and fifth hybridization sequences.

Embodiments of the system may also include that the probe is configured to be in an equilibrium between formation of the second and third duplexes and formation of the recognition duplex.

Embodiments of the system may also include that in the absence of binding of the DNA binding protein to the recognition duplex, the equilibrium is shifted towards the formation of the second and third duplexes.

Embodiments of the system may also include that in the presence of binding of the DNA binding protein to the recognition duplex, a DNA binding protein-probe hybrid is formed and the equilibrium is shifted towards the formation of the recognition duplex.

Embodiments of the system may also include that in the presence of a single-stranded DNA sequence that stabilizes the DNA binding protein-probe hybrid, the equilibrium is shifted towards the formation of the recognition duplex.

Embodiments of the system may also include that the DNA binding protein has a concentration ranging from 1 nM to 1 $\mu$M.

Embodiments of the system may also include that the first signaling moiety includes a fluorophore and the second signaling moiety includes a quencher.

Embodiments of the system may also include that the first signaling moiety includes a fluorophore and the second signaling moiety includes a second fluorophore.

Embodiments of the system may also include that the first signaling moiety includes an electrochemical reporter and the second signaling moiety includes an electrode.

Embodiments of the system may also include that the first signaling moiety includes a nanoparticles (gold, silver or diamonds) and the second signaling moiety includes a quencher or a second nanoparticles.

Embodiments of the system may also include that the probe is immobilized on the surface of the electrode.

Embodiments of the system may also include that the first signaling moiety includes a macromolecule that display a catalytic activity and the second signaling moiety includes an inhibitor or an activator of this catalytic activity.

Embodiments of the system may also include that the system includes an array of probes.

Aspects of the present disclosure also include a method of detecting a DNA binding protein in a sample. The method includes contacting a unimolecular oligonucleotide probe with the sample, whereby the DNA binding protein selectively binds to the recognition duplex to form a DNA binding protein-probe hybrid. The method further includes detecting the presence or absence of the DNA binding protein-probe hybrid.

Embodiments of the method may also include that the detecting includes quantifying the concentration of the DNA binding protein-probe hybrid by comparing the signal from the sample to: (1) a saturating concentration of a competitive DNA binding sequence; (2) a saturating concentration of a transcription factor; or (3) a saturating concentration of a single-stranded DNA configured to stabilize the DNA binding protein-probe hybrid.

Embodiments of the method may also include that the sample includes a complex sample.

Embodiments of the method may also include that the sample includes whole blood.

Embodiments of the method may also include that the sample includes a crude nuclear extract.

BRIEF DESCRIPTION OF THE FIGURES

FIG. 5 also shows graphs of fluorescence vs. temperature and fluorescence vs. wavelength (nm) for modular probes, according to embodiments of the present disclosure.

FIG. 6 (bottom) shows a schematic of the signaling of the modular probe (e.g., the probe stem opening) in the presence of two targets binding to a single probe, according to embodiments of the present disclosure.

FIG. 7 (bottom) shows graphs of fluorescence vs. wavelength (nm) in buffer and whole blood (panels a and b), according to embodiments of the present disclosure.

FIG. 13 (bottom) shows a schematic (FIG. 13(a)) and graph (FIG. 13(b)) for the quantification of transcription factors in crude nuclear extracts using a probe, according to embodiments of the present disclosure.

FIG. 14(a) shows a graph of square wave voltammograms for TATA binding protein probe in the presence of various concentration of TATA binding protein, according to embodiments of the present disclosure (results were obtained in buffer). FIG. 14(b) shows a graph of current signal vs. target concentration for TATA binding protein probes, according to embodiments of the present disclosure (results were obtained in buffer and in 250 µg/mL of HeLa nuclear extracts).

Figure 1:
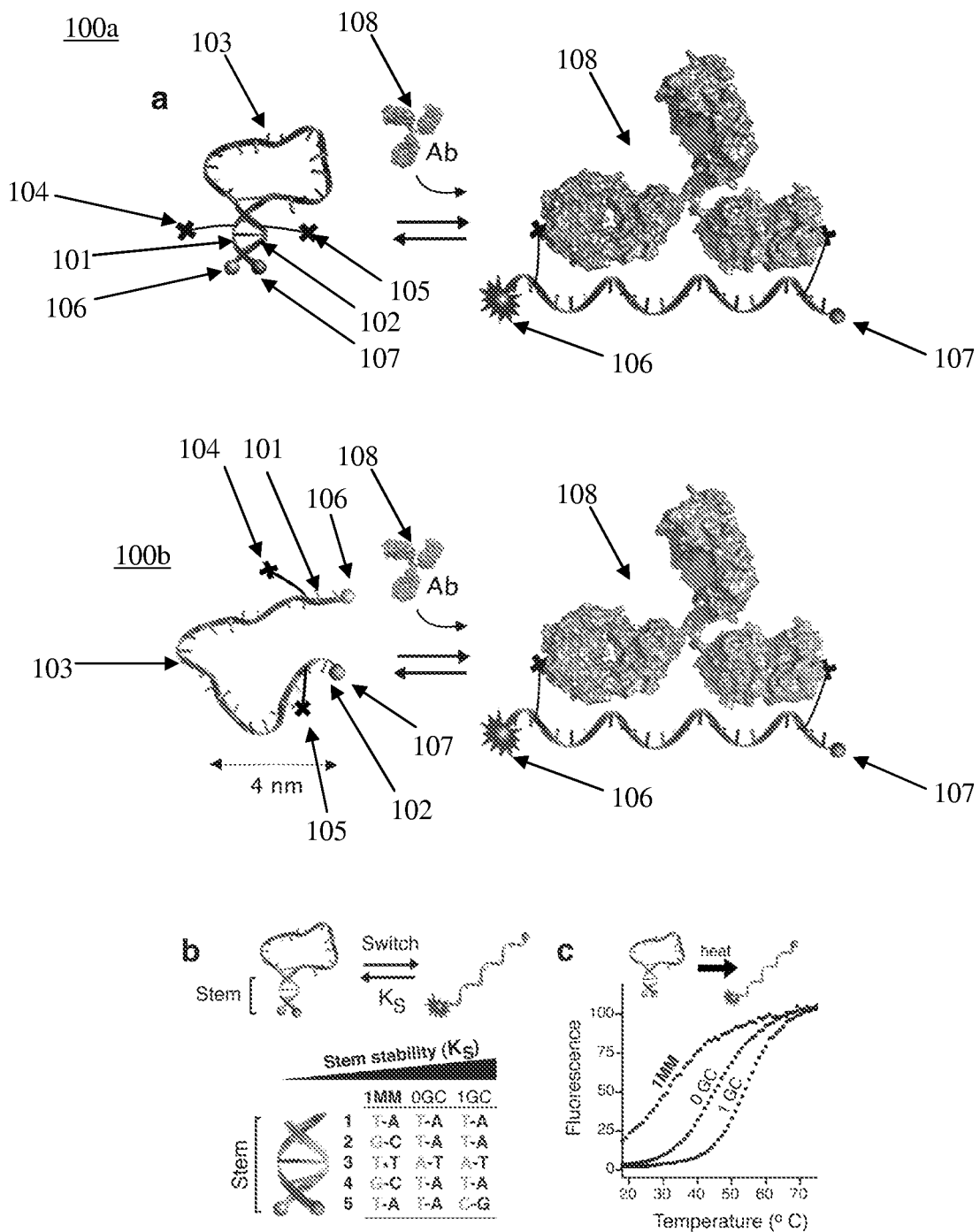
FIG. 1(a) shows a unimolecular oligonucleotide probe (top: with stem; bottom: without stem) configured to produce a detectable signal upon target binding, according to embodiments of the present disclosure.
FIG. 1(b) shows a chart of stem nucleotide sequence vs. stem stability for probes according to embodiments of the present disclosure.
FIG. 1(c) shows a graph of fluorescence intensity vs. temperature for probes according to embodiments of the present disclosure.

Before the present invention is described in greater detail, it is to be understood that this invention is not limited to the particular embodiments described, and as such may, of course, vary. It is also to be understood that the terminology used herein is for the purpose of describing particular embodiments only, and is not intended to be limiting, since the scope of the present invention is embodied by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, it will be readily apparent to one of ordinary skill in the art in light of the teachings herein that certain changes and modifications may be made thereto without departing from the spirit and scope of the appended claims. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. To the extent such publications may set out definitions of a term that conflicts with the explicit or implicit definition of the present disclosure, the definition of the present disclosure controls. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS

Provided are unimolecular oligonucleotide probes for detecting a target in a sample. The probes use target binding-induced structural changes to detect the presence of the target in the sample. Also provided are methods of using the probes to detect a target in a sample.

Below, the subject systems that include the oligonucleotide probes are described first in greater detail, followed by a review of the various methods in which the probes may find use, as well as a discussion of various representative applications in which the subject probes and methods find use.

Systems

Systems of the present disclosure include one or more oligonucleotide probes described in more detail below. The term "probe" as used herein refers to a unimolecular biopolymer that undergoes a structural change upon its specific binding to a target (e.g., molecule, macromolecule, or analyte). Probes may include, but are not limited to, nucleic acids (DNA or RNA), non-natural oligonucleotide analogs such as PNA, LNA, aptamers, peptides and proteins, etc. In some instances, the probes are oligonucleotides that may be of any length, but may be short oligonucleotides ranging from 20 to 100 nucleotides, or 25 to 90 nucleotides, such as 30 to 80 nucleotides. The particular use of terms "nucleic acid," "oligonucleotide," and "polynucleotide" should in no way be considered limiting and may be used interchangeably herein. "Oligonucleotide" is used when the relevant nucleic acid molecules include less than about 100 bases. "Polynucleotide" is used when the relevant nucleic acid molecules include more than about 100 bases. Both terms are used to denote DNA, RNA, modified or synthetic DNA or RNA (including but not limited to nucleic acids comprising synthetic and naturally-occurring base analogs, dideoxy or other sugars, thiols or other non-natural or natural polymer backbones), or other nucleobase containing polymers. Accordingly, the terms should not be construed to define or limit the length of the nucleic acids referred to and used herein.

Oligonucleotides of the present disclosure may be single-stranded, double-stranded, triple-stranded, or include a combination of these conformations. Generally oligonucleotides contain phosphodiester bonds, although in some cases, as outlined below, nucleic acid analogs are included that may have alternate backbones, comprising, for example, phosphoramide, phosphorothioate), phosphorodithioate, O-methylphosphoroamidite linkages, and peptide nucleic acid backbones and linkages. Other analog nucleic acids include those with positive backbones, non-ionic backbones, and non-ribose backbones. Nucleic acids containing one or more carbocyclic sugars are also included within the definition of nucleic acids. These modifications of the ribose-phosphate backbone may be done to facilitate the addition of additional moieties such as labels, or to increase the stability and half-life of such molecules in physiological environments. The term "nucleic acid sequence" or "oligonucleotide sequence" refers to a contiguous string of nucleotide bases and in particular contexts also refers to the particular placement of nucleotide bases in relation to each other as they appear in an oligonucleotide.

In certain embodiments, the probes may recognize their targets by specific binding of the target to the probe at, for example, a target binding moiety included on the probe. "Target" refers to any molecule that specifically binds to a probe of the present disclosure. These include, but are not limited to, macromolecules (e.g., proteins, carbohydrates, nucleic acids, lipids, etc.), small molecules (e.g., peptides, aptamers, etc.), and the like. While not an exhaustive list, in certain embodiments, the target may be an antibody, a DNA binding protein, a receptor, or an enzyme that specifically binds the probe. One of skill in the art will recognize that the important aspect of probe-target binding is not the particular mechanism involved but the fact that the binding is specific, as in specifically binding as defined in this disclosure.

Oligonucleotide probes of the present disclosure may be unimolecular. By "unimolecular" is meant that the probe includes a single moiety that binds to the target. Unimolecular probes do not include probes that include two or more separate probe elements that associate with each other during formation of the target-probe hybrid. Unimolecular probes may include single-stranded oligonucleotide probes, as well as single-stranded oligonucleotide probes that are directly or indirectly bound to target binding moieties as described in detail herein.

In certain embodiments, the target is a bidentate target. As used herein, "denticity" refers to the number of distinct binding sites included in a target molecule. A polydentate target may bind to two or more target binding moieties, with each target binding moiety binding to different binding sites on the target. For example, a bidentate target includes two target binding sites with each binding site capable of specifically binding to a target binding moiety. Bidentate targets may include, but are not limited to, antibodies which may include two antigen binding sites that each specifically bind to one copy of a specific antigen. In certain embodiments, the target is a non-bidentate target, for example a target that includes one binding site capable of specifically binding to a target binding moiety.

Aspects of the present disclosure include oligonucleotide probes for detecting a target in a sample. The probes can be made as oligonucleotide strands constructed using techniques well-known to those of skill in the art, and include internal sequences allowing the oligonucleotide strand to undergo intramolecular hybridization when one internal hybridization sequence specifically hybridizes to a complementary internal hybridization sequence.

The terms "complementary" or "complementarity" refer to polynucleotides (i.e., a sequence of nucleotides) related by base-pairing rules. For example, the sequence "5'-AGT-3'," is complementary to the sequence "5'-ACT-3'". Complementarity may be "partial," in which only some of the nucleic acids' bases are matched according to the base pairing rules, or there may be "complete" or "total" complementarity between the nucleic acids. The degree of complementarity between nucleic acid strands can have effects on the efficiency and strength of hybridization between nucleic acid strands under defined conditions.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the thermal melting point, $T_m$, of the formed hybrid. Hybridization methods involve the annealing of one nucleic acid to another, complementary nucleic acid, e.g., a nucleic acid having a complementary nucleotide sequence.

Hybridization is carried out in conditions permitting specific hybridization. The length of the complementary sequences and GC content affects the thermal melting point, $T_m$, of the hybridization conditions necessary for obtaining specific hybridization of the target site to the target nucleic acid. Hybridization may be carried out under stringent conditions. The phrase "stringent hybridization conditions" refers to conditions under which a probe will hybridize to its target subsequence, typically in a complex mixture of nucleic acid, but to no other sequences at a detectable or significant level. Stringent conditions are sequence-dependent and may be different in different circumstances. The phrase "selectively (or specifically) hybridizing" refers to the binding, duplexing, or hybridizing of a molecule only to a particular nucleotide sequence under stringent hybridization conditions when that sequence is present in a complex mixture (e.g., total cellular, library DNA or RNA, complex samples such as whole blood samples and the like). Those of ordinary skill in the art will readily recognize that alternative hybridization and wash conditions can be utilized to provide conditions of similar stringency and will recognize that the combination of parameters may be more important than the measure of any single parameter.

Intramolecular hybridization of the oligonucleotide probes can result in the probe taking a stem-loop secondary conformation in the absence of target binding to the probe. The probes are configured to use target binding-induced structural changes to detect the presence of the target in the sample. As used herein, the different oligonucleotide probe structures, such as those that exist in the presence or absence of a target, may be as referred to as "conformations." In certain embodiments, internal hybridization sequence lengths range from 5 to 25 nucleotides, for example 5 to 20 nucleotides, such as 10 to 20 nucleotides per internal hybridization sequence. The "loop" structures of each probe may be of any length suitable to the application, but may range from 3 to 30 nucleotides in length, for example 5 to 25 nucleotides, such as 10 to 20 nucleotides in length.

In some embodiments the hybridization leads to two double-stranded oligonucleotides separated by a single-stranded region. The single-stranded region of each probe may be of any length suitable to the application, but may range from 3 to 30 nucleotides in length, for example 5 to 25 nucleotides, such as 10 to 20 nucleotides in length.

The probes may be provided in solution. In these cases, the probes are free to diffuse through the solution and are not attached to a surface. In certain embodiments, the probes are attached to the surface of a substrate. The probes may be attached to the surface of the substrate at predetermined locations, such that the probes are arranged in an array formation. An "array," includes any one-dimensional, two-dimensional or substantially two-dimensional (as well as a three-dimensional) arrangement of addressable regions bearing a particular probe associated with that region. The probes may be covalently attached to the arrays at any point along the nucleic acid chain. In certain cases, the probes are attached at one of their termini (e.g., the 3' or 5' terminus). In some cases, the probes are attached to the array at an internal site of the probe. An "addressable array" includes any one or two dimensional arrangement of discrete regions (or "features") bearing particular probes associated with that region and positioned at particular predetermined locations on the substrate (each such location being at a known "address"). These regions may or may not be separated by intervening spaces.

Any given substrate may carry one, two, four or more arrays disposed on a front surface of the substrate. Depending upon the use, any or all of the arrays may be the same or different from one another and each may contain multiple spots or features. A typical array may contain more than ten, more than one hundred, more than one thousand, more than ten thousand features, or even more than one hundred thousand features, in an area of less than 20 cm$^2$, such as less than 10 cm$^2$. For example, features may have widths (that is, diameter, for a round spot) in the range from a 10 μm to 1.0 cm. In other embodiments each feature may have a width in the range of 1.0 μm to 1.0 mm, such as 5.0 μm to 500 μm, including 10 μm to 200 μm. Non-round features may have area ranges equivalent to that of circular features with the foregoing width (diameter) ranges. In certain embodiments, the arrays are formed by processes involving drop deposition of reagents, for example, photolithographic array fabrication processes may be used.

With arrays that are read by detecting fluorescence, the substrate may be of a material that emits low fluorescence upon illumination with the excitation light. Additionally in this situation, the substrate may be relatively transparent to reduce the absorption of the incident illuminating light (e.g., laser light) and subsequent heating if the focused light travels too slowly over a region.

Oligonucleotide Probes

In certain embodiments, the oligonucleotide probes are configured to produce a detectable signal when a target specifically binds to the probe to form a target-probe hybrid. The target may specifically recognize and bind to particular portions of the probe at, for example, a target binding moiety included on the probe. As used herein, the term "target binding moiety" refers to any molecule that specifically binds a target of the present disclosure. These include, but are not limited to, proteins, peptides, carbohydrates, nucleic acids, lipids, small molecules, and the like. For instance, the target binding moiety may be an antigen. In some cases, the probe includes two target binding moieties, such as a first target binding moiety and a second target binding moiety. The first target binding moiety may be different from the second target binding moiety, for example in embodiments where the target is capable of binding to two or more different target binding moieties. In certain instances, the first target binding moiety and the second target binding moiety are substantially the same, for example in embodiments where the target is capable of binding two or more of the same target binding moiety, such as where the target is an antibody.

The target binding moiety may be bound to the probe. In some cases, the target binding moiety is directly bound to the probe. For example, the target binding moiety may be directly bound to the probe by modification of a nucleotide in the oligonucleotide strand that makes up the probe, such as, but not limited to, covalent attachment of the target binding moiety to a nucleotide in the oligonucleotide sequence, insertion of the target binding moiety between two nucleotides in the oligonucleotide sequence through the introduction of additional phosphodiester bonds, and the like.

In some cases, the target binding moiety is indirectly bound to the probe, such as, but not limited to, attachment of the target binding moiety to the probe through a linker moiety. The linker moiety can be any linker moiety suitable for the attachment of the target binding moiety to one or more nucleotides in the oligonucleotide probe. The linker moiety may include 1 to 25 carbons, such as 2 to 20 carbons, including 5 to 15 carbons. In certain embodiments, the target binding moiety is indirectly bound to the probe by hybridization of an oligonucleotide to the probe. In these embodiments, the target binding moiety may be attached either directly or indirectly to a hybridization sequence, which specifically hybridizes to a complementary sequence on the probe to form a duplex. As indicated above, certain embodiments of the probe include two target binding moieties. In some cases, the first target binding moiety and the second target binding moiety are attached to hybridization sequences that have different nucleotide sequences. In these cases, the hybridization sequences specifically hybridize to different complementary sequences on the probe. In other instances, the first target binding moiety and the second target binding moiety are attached to hybridization sequences that have substantially the same nucleotide sequence. In these instances, the hybridization sequences specifically hybridize to the same complementary nucleotide sequence. The probe may include one or more, such as two or more repeats of the complementary nucleotide sequence, such that a corresponding number of hybridization sequences may be hybridized to the probe, and thus a corresponding number of target binding moieties may be attached to the probe. In certain embodiments, the probe includes two hybridization sequences that are complementary to the hybridization sequences bound to the target binding moieties, such that two target binding moieties are attached to the probe. In some cases, the probe includes a frame inversion between the hybridization sequences. The frame inversion may be a 3' to 3' or a 5' to 5' frame inversion. Inclusion of a frame inversion may facilitate attachment of the target binding moieties to the probe in a configuration that facilitates the structural change induced by the binding of the target to both of the target binding moieties.

In some embodiments, the probe also includes two or more hybridization sequences (e.g., intramolecular hybridization sequence, IHS) configured to allow the oligonucleotide strand to undergo intramolecular hybridization. For instance, the probe may include a first hybridization sequence (e.g., a first IHS) and a second hybridization sequence (e.g., a second IHS). In embodiments that include two target binding moieties, as described herein, the first hybridization sequence and the second hybridization sequence may be configured to form a duplex in the absence of target binding to both of the target binding moieties. The first hybridization sequence and the second hybridization sequence may be separated by a loop structure formed by the oligonucleotide sequence of the probe that is between the first hybridization sequence and the second hybridization sequence. As such, in the absence of target binding to the target binding moieties, the probe may adopt a stem-loop conformation.

In some embodiments, the probe may include two double-stranded regions separated by a single-stranded region. The single-stranded region may facilitate an increase in the flexibility of the probe in the absence of target binding.

The probes also include one or more signaling moieties. In some cases, the probe includes two signaling moieties, such as a first signaling moiety and a second signaling moiety. In certain embodiments, the first signaling moiety is held at distance in close proximity to the second signaling moiety, such as adjacent the second signaling moiety, by complementary base-pairing within the probe. In some embodiments, the probe is flexible in the absence of target binding, allowing the signaling moieties to approach one another transiently or intermittently. In embodiments of the probe configured to produce a detectable change in signal in the presence of target binding to the target binding moieties, under conditions in the absence of target, the distance the first signaling moiety is held from the second signaling moiety is sufficient to minimize, suppress, or prevent the first signaling moiety from emitting a detectable signal. In some embodiments, this proximity instead enhances or maximizes the detectable signal from the first signaling moiety. In some embodiments, collisions between the two signaling moieties increase or decrease the signal or signals associated with them. When target is present and binds to the target binding moieties of the probe, the internal hybridization of the probe is disrupted. Disruption of the internal hybridization allows the end of the nucleotide chain to which the first signaling moiety is attached to move to a distance further away from the second signaling moiety. Under conditions in the presence of target, the distance the first signaling moiety moves away from the second signaling moiety is sufficient to lead to a detectable change in the signal from the first signaling moiety. In some embodiments, this change in distance leads to a detectable decrease in signal. In other embodiments, target binding prevents collisions between the two signaling moieties, leading to a detectable change in their signal.

As described above, in the absence of target binding to the target binding moieties, the probe may be in a stem-loop configuration. In these cases, the probe may adopt a conformation where the first signaling moiety is positioned adjacent the second signaling moiety, such that the probe does not produce a detectable signal. For example, the first signaling moiety may be a fluorophore and the second signaling moiety may be a quencher. In these instances, under conditions in the absence of target, the distance the fluorophore is held from the quencher is sufficient to minimize, suppress, or prevent the fluorophore from emitting a detectable signal. Alternatively, this proximity may increase the signal from the first signaling moiety. When target is present and binds to the target binding moieties of the probe, the internal hybridization of the probe is disrupted such that the fluorophore is able to move to a distance further away from the quencher. Under conditions in the presence of target, the distance the fluorophore moves away from the quencher is sufficient to allow the signal emitted by the fluorophore to change detectably. In some instances, the detectable change in signal is an increase in the signal emitted by the fluorophore.

As described above, in the absence of target binding to the target binding moieties, the probe may have a flexible conformation. In these cases, the first signaling moiety can transiently collide with or bind to the second signaling moiety, such the signal from the signaling moieties is changed. For example, the first signaling moiety may be a fluorophore and the second signaling moiety may be a quencher. In these instances, under conditions in the absence of target, collisions between the fluorophore and the quencher are sufficient to minimize, suppress, or prevent the fluorophore from emitting a detectable signal. When target is present and binds to both the target binding moieties of the probe, contact between the fluorophore and the quencher may be inhibited or reduced such that the quencher does not approach the fluorophore as readily or as frequently. Under conditions in the presence of target, the distance the fluorophore moves away from the quencher detectably changes the signal that the fluorophore emits. In certain cases, the detectable change in signal is an increase in the signal emitted by the fluorophore.

The term "fluorophore" refers to any molecular entity that is capable of absorbing energy of a first wavelength and re-emit energy at a different second wavelength. In certain embodiments, the oligonucleotide probe includes a fluorophore attached to one end of the probe or at a central position in the probe sequence, so long as the position of the fluorophore allows the fluorophore to be positioned adjacent the quencher in the absence of target binding to the target binding moieties and away from the quencher when target binds to the target binding moieties. In some embodiments, as discussed in more detail below, the fluorophore may be attached to one end of the probe. The fluorophore attached to the probe need not be a single molecule, but may include multiple molecules. In some embodiments, the fluorophore is a fluorescent moiety, such as but not limited to, a fluorescent nanoparticle, such as gold, silver or diamond nanoparticles, and the like. The "end" of the oligonucleotide probe possessing the fluorophore includes any nucleotide within one quarter of the total number of nucleotides in the probe from the terminal nucleotide. Alternatively, the end possessing the fluorophore includes the terminal 10, 9, 8, 7, 6, 5, 4, 3 or 2 nucleotides of the probe. Attachment may also be on the terminal nucleotide alone. The attachment of the fluorophore to the oligonucleotide probe allows the fluorophore to be positioned in an alternate configuration at a distance away from the quencher in response to target specifically binding the probe, thereby generating a detectable signal.

The fluorophore may be synthetic or biological in nature, as known to those of skill in the art. More generally, any fluorophore can be used that is stable under assay conditions and that can be sufficiently suppressed when in close proximity to the quencher such that a significant change in the intensity of fluorescence of the fluorophore is detectable in response to target specifically binding the probe. Examples of suitable fluorophores include, but are not limited to CAL Fluor Red 610 (FR610; Biosearch Technologies, Novato, Calif.), fluorescein isothiocyanate, fluorescein, 6-carboxyfluorescein (6-FAM), rhodamine and rhodamine derivatives, coumarin and coumarin derivatives, cyanine and cyanine derivatives, Alexa Fluors (Molecular Probes, Eugene, Oreg.), DyLight Fluors (Thermo Fisher Scientific, Waltham, Mass.), and the like.

The term "quencher" may refer to a substance that absorbs excitation energy from a fluorophore and dissipates that energy as heat. The quencher may also absorb excitation energy from a fluorophore and dissipate that energy as re-emitted light at a different wavelength. Quenchers are used in conjunction with fluorophores, such that when the quencher is positioned adjacent the fluorophore or at a distance sufficiently close to the fluorophore, the emission of the fluorophore is suppressed. However, when the quencher is positioned away from the fluorophore or at a distance sufficiently far from the fluorophore, the emission of the fluorophore is not suppressed, such that a signal of the fluorophore is detectable. Alternatively, the quencher may include moieties that reduce the emission of the fluorophore via photoelectron transfer, resonance energy transfer or other quenching mechanisms. The quencher may also be replaced by a second fluorophore capable of resonance energy transfer, by a second fluorophore capable of forming an excimer or exiplex or, in general, by any other group that modulates the fluorescence of the first fluorophore.

The oligonucleotide probes may include a quencher attached at a central position away from the ends of the probe (e.g., at a position in the central portion of the probe sequence) or at one end of the probe, as long as the position of the fluorophore allows the fluorophore to be positioned adjacent to the quencher in the absence of target binding to the target binding moieties and away from the quencher when target binds to the target binding moieties. The quencher attached to the probe need not be a single molecule, but may include multiple molecules. The attachment position of the quencher includes any nucleotide within the probe that positions the quencher in close proximity to the fluorophore in the absence of target specifically binding to the target binding moieties. The attachment of the quencher to the oligonucleotide probe allows the quencher to be positioned in an alternate configuration at a distance away from the fluorophore in response to target specifically binding the probe, thereby detectably changing the signal emitted by the fluorophore. In certain instances, the detectable change in the signal is an increase in the signal emitted by the fluorophore.

The quencher may be synthetic or biological in nature, as known to those of skill in the art. More generally, any quencher can be used that is stable under assay conditions and that can sufficiently suppress the fluorescence of the fluorophore when in close proximity to the fluorophore such that a significant change in the intensity of fluorescence of the fluorophore is detectable in response to target specifically binding the probe. Examples of quenchers include, but are not limited to, Black Hole Quencher (BHQ; Biosearch Technologies, Novato, Calif.), Dabsyl (dimethylaminoazosulphonic acid), Qxl quenchers (AnaSpec Inc., San Jose, Calif.), Iowa black FQ, Iowa black RQ, and the like. In another embodiment the quencher may also be fluorescent, leading to emission at a second wavelength when the quencher is in proximity to the first fluorophore. Examples of such fluorophore/quencher pairs include Alexa488-Alexa555, Alexa488-Cy3, Cy3-Cy5. In other embodiments, the quencher is a second fluorophore that forms an excimer or an exciplex with the first fluorophore, leading to a change in fluorescence upon their segregation. An example would include an embodiment in which both the fluorophore and the quencher are pyrene.

In certain embodiments, the probes of the present disclosure are oligonucleotides that include a first signaling moiety that includes a macromolecule having a catalytic activity and a second signaling moiety that includes an inhibitor (or an activator) of the catalytic activity. In certain embodiments, the catalytic macromolecule is held at distance in close proximity to the inhibitor, such as adjacent the inhibitor, by complementary base-pairing within the probe. In embodiments of the probe configured to produce a detectable change in signal in the presence of target binding to the target binding moieties, under conditions in the absence of target, the distance the catalytic macromolecule is held from the inhibitor is sufficient to minimize, suppress, or prevent the catalytic macromolecule from performing its catalytic activity. In some embodiments, such as where the second signaling moiety is an activator, this proximity instead enhances or maximizes the catalytic activity of the catalytic macromolecule. When target is present and binds to the target binding moieties of the probe, the internal hybridization of the probe is disrupted. Disruption of the internal hybridization allows the end of the nucleotide chain to which the catalytic macromolecule is attached to move to a distance further away from the inhibitor. Under conditions in the presence of target binding, the distance the catalytic macromolecule moves away from the inhibitor is sufficient to lead to a detectable change in the catalytic activity of the catalytic macromolecule. In some embodiments, this change in distance leads to a detectable increase in signal.

In certain embodiments, the target may be removed and the probe regenerated using mild conditions that retain the integrity of the probe and allow the probe to re-establish the internal base pair hybridization pattern that suppresses the fluorescence of the fluorophore. In these embodiments, the probes are reusable, such that the probes may be regenerated as described above and reused any number of times, such as 2 or more times, including 3 or more times, for instance 5 or more times, or 10 times or more, while maintaining substantially the same ability to detect a target in a sample.

In certain embodiments, the probes are capable of specifically identifying nanomolar or picomolar concentrations of targets in a sample. For example, the probes may be configured to detect a target in a sample, where the target has a concentration ranging from 1 pM to 100 nM, such as from 1 pM to 750 pM, including from 5 pM to 500 pM, or from 10 pM to 300 pM. In some instances the probes may be configured to detect a target in a sample, where the target has a concentration ranging from 1 nM to 1 µM, such as from 1 nM to 750 nM, including from 1 nM to 500 nM, or from 1 nM to 250 nM, for instance from 1 nM to 100 nM.

The phrase binding "specifically" or "selectively," refers to the interaction of an oligonucleotide probe, as described herein, with a specific target in a manner that is determinative of the presence of the target in the presence or absence of a heterogeneous population of molecules that may include nucleic acids, proteins, and other biological molecules. Thus, under designated conditions, a specified oligonucleotide probe binds to a particular target and does not bind in a significant manner to other molecules in the sample. Probes do not bind to a molecule in a detectable or significant manner when the interaction does not disrupt the intramolecular hybridization of the probe resulting in no significantly detectable signal or no significantly detectable change in signal from the probe.

Moreover, "specific binding" results in a disruption of intramolecular hybridization between probe nucleotide sequences resulting in a conformational change in the probe such that the probe produces a detectable signal or a detectable change in a signal. Thus, specific binding may be determined by titration of the probe with a target. Specific binding will allow an increase (or decrease) in signal with increasing amount of target contacted with the probe.

Probes that Use Binding-Induced Segregation of Two Target Binding Moieties

An example of an oligonucleotide probe 100a configured to produce a detectable signal upon target binding-induced segregation of two target binding moieties is depicted in FIG. 1. An aspect of the oligonucleotide probe of FIG. 1(*a*, top) is that the probe 100a has a stem-loop structure formed by intramolecular hybridization of a single-stranded oligonucleotide. In other embodiments, the probe 100b may be stemless (FIG. 1(*a*, bottom)). In these embodiments, the probe 100b may have a lower gain than a probe that includes a stem due to an increase in the fluorescence background in the absence of target (FIG. 1(*a*, bottom)). In embodiments that include a step-loop structure, the stem-loop structure of the probe 100a is formed through intramolecular hybridization between a first hybridization sequence 101 and a second hybridization sequence 102. Internal hybridization between first hybridization sequence 101 and second hybridization sequence 102 forms a duplex. First hybridization sequence 101 and second hybridization sequence 102 are separated by a loop structure 103 formed by the oligonucleotide sequence between first hybridization sequence 101 and second hybridization sequence 102.

Regardless of whether the probe does or does not include a stem-loop structure, the oligonucleotide probe also includes a first target binding moiety 104 and a second target binding moiety 105. The first target binding moiety 104 and the second target binding moiety 105 may be directly or indirectly attached to the probe as described above. The oligonucleotide probe further includes a fluorophore 106 and a quencher 107. In FIG. 1, the fluorophore 106 is coupled to one end of the oligonucleotide strand of the probe and the quencher 107 is coupled to the other end of the oligonucleotide strand of the probe. As described herein, the fluorophore and/or the quencher may be coupled to the oligonucleotide strand of the probe at an internal site. As shown in FIG. 1(a), in the absence of target binding to the target binding moieties (104 and 105), the internal hybridization between the first and second hybridization sequences (101 and 102) positions the fluorophore 106 adjacent the quencher 107, such that the quencher 107 substantially suppresses detectable emissions from the fluorophore 106 (see FIG. 2). As shown in FIG. 1(a), binding of the target 108 (e.g., an antibody) to the first and second target binding moieties (104 and 105) causes a conformational change in the probe that positions the fluorophore 106 at a distance away from the quencher 107, such that the fluorophore 106 produces a detectable signal (see FIG. 2).

In certain examples, the length of each stem duplex structure may be different, as is also the case with loop structures. Limits on the size of each duplex, each loop, and the single-stranded linear probe length are not contemplated as being rigidly limited but are rather application dependent. Optimal lengths for each of the probe components described herein may be determined without undue experimentation by one of skill in the art through the teachings of this specification. Lengths provided herein are examples only.

In certain embodiments, the probe is configured to have switching thermodynamics (or equilibrium) between the non-bound state (e.g., stem-loop structure) and the target bound state where the equilibrium is shifted to the non-bound state (e.g., stem-loop structure) in the absence of target binding (see FIG. 1(b)), without over-stabilizing this structure. Over-stabilization of the stem-loop may favor the binding of two targets, one on each of the target binding moieties on a probe, thus precluding opening of the stem and the signaling of the probe. FIGS. 1(b) and 1(c) present different variants of probes with various switching thermodynamics that are optimized for different temperatures.

Figure 4:
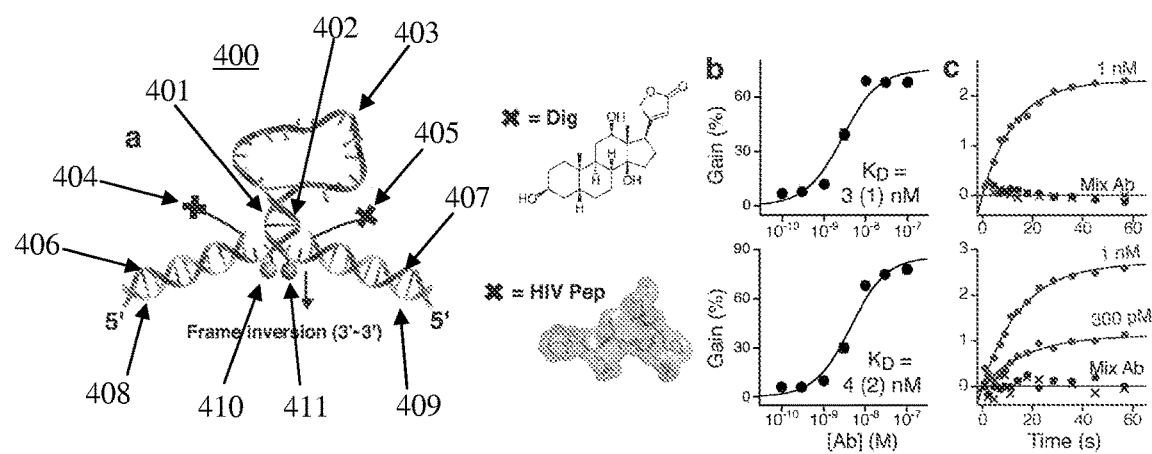
FIG. 4(a) shows a modular oligonucleotide probe configured to produce a detectable fluorescent signal upon target binding, according to embodiments of the present disclosure. The fluorescent signaling moieties are FAM-6 for the fluorophore and BHQ-1 for the quencher. In this particular probe, the first and second binding moieties (X) are attached to the probe via hybridization to third and fourth hybridization sequences.
FIG. 4(b) shows graphs of fluorescent signal vs. target concentration for modular anti-Dig antibody and anti-DNP antibody probes according to embodiments of the present disclosure.
FIG. 4(c) shows graphs of the fluorescent signal vs. time for modular anti-Dig antibody and anti-DNP antibody probes according to embodiments of the present disclosure.

Another example of an oligonucleotide probe 400 configured to produce a detectable signal upon target binding is depicted in FIG. 4. Embodiments of probe 400 include the modular attachment of the first target binding moiety 404 and the second target binding moiety 405 to the probe. An aspect of the modular oligonucleotide probe of FIG. 4 is that the probe has a stem-loop structure formed by intramolecular hybridization of a single-stranded oligonucleotide. This stem-loop structure is formed through intramolecular hybridization between a first hybridization sequence 401 and a second hybridization sequence 402. Internal hybridization between first hybridization sequence 401 and second hybridization sequence 402 forms a duplex. First hybridization sequence 401 and second hybridization sequence 402 are separated by a loop structure 403 formed by the oligonucleotide sequence between first hybridization sequence 401 and second hybridization sequence 402.

The oligonucleotide probe also includes a first target binding moiety 404 and a second target binding moiety 405. The probe 400 also includes third hybridization sequence 406 and fourth hybridization sequence 407. The first target binding moiety 404 is attached to a fifth hybridization sequence 408, and the second target binding moiety 405 is attached to a sixth hybridization sequence 409. As depicted in FIG. 4(a), the first target binding moiety 404 and the second target binding moiety 405 are indirectly attached to the probe by hybridization between third hybridization sequence 406 and fifth hybridization sequence 408, and by hybridization between fourth hybridization sequence 407 and sixth hybridization sequence 409, respectively.

The oligonucleotide probe 400 further includes a fluorophore 410 and a quencher 411. In FIG. 4, the fluorophore 410 and the quencher 411 are coupled to the oligonucleotide strand of the probe at internal sites. As described herein, the fluorophore and/or the quencher may be coupled to the oligonucleotide strand of the probe at other sites, such as at or near the end of the oligonucleotide strand of the probe. As shown in FIG. 4(a), in the absence of target binding to the target binding moieties (404 and 405), the internal hybridization between the first and second hybridization sequences (401 and 402) positions the fluorophore 410 adjacent the quencher 411 such that the quencher 411 substantially suppresses detectable emissions from the fluorophore 410 (see FIG. 4(b)). Binding of the target to the first and second target binding moieties (404 and 405) causes a conformational change in the probe 400 that positions the fluorophore 410 at a distance away from the quencher 411, such that the fluorophore 410 produces a detectable signal (see FIG. 4(b)).

Probes that Utilize Binding-Induced Reconstitution of Recognition Elements

Aspects of the present disclosure also include an oligonucleotide probe for the detection and quantification of a DNA binding protein in a sample. In some cases, the probe includes two or more recognition sequences, such as a first recognition sequence and a second recognition sequence. The first recognition sequence and the second recognition sequence may be complementary hybridization sequences. In certain instances, the first recognition sequence and the second recognition sequence are configured to form a recognition duplex by intramolecular hybridization of the first recognition sequence to the second recognition sequence. The target DNA binding protein may specifically recognize and bind to particular portions of the probe, at for example the recognition duplex.

The probe also includes two or more hybridization sequences (e.g., intramolecular hybridization sequence, 1HS) configured to allow the oligonucleotide strand to undergo intramolecular hybridization. For instance, the probe may include a first hybridization sequence (e.g., a first IHS) and a second hybridization sequence (e.g., a second IHS). The first hybridization sequence and the second hybridization sequence may be configured to form a second duplex in the absence of binding of the DNA binding protein to the recognition duplex. The first hybridization sequence and the second hybridization sequence may be separated by a loop structure formed by the oligonucleotide sequence of the probe that is between the first hybridization sequence and the second hybridization sequence. As such, in the absence of binding of the DNA binding protein to the recognition duplex, the probe may adopt a stem-loop conformation.

In addition, the probe includes a third hybridization sequence and a fourth hybridization sequence (e.g., third and fourth intramolecular hybridization sequences; a third IHS and a fourth IHS). The third hybridization sequence and the fourth hybridization sequence may be configured to allow the oligonucleotide strand to undergo an additional intramolecular hybridization. For instance, the third hybridization sequence and the fourth hybridization sequence may be configured to form a third duplex in the absence of binding of the DNA binding protein to the recognition duplex. The third hybridization sequence and the fourth hybridization sequence may be separated by a second loop structure formed by the oligonucleotide sequence of the probe that is between the third hybridization sequence and the fourth hybridization sequence. As such, in the absence of binding of the DNA binding protein to the recognition duplex, the probe may adopt a double stem-loop conformation.

In certain embodiments, the probe is configured to produce a detectable signal when contacted with the target DNA binding protein. In some instances, the probe includes one or more signaling moieties. For example, the probe may include two signaling moieties, such as a first signaling moiety and a second signaling moiety. In certain embodiments, the first signaling moiety is held at distance in close proximity to the second signaling moiety, such as adjacent the second signaling moiety, by complementary intramolecular base-pairing within the probe as described above (e.g., by formation of the second and third duplexes to produce a probe with a double stem-loop conformation). Under conditions in the absence of the DNA binding protein, the distance the first signaling moiety is held from the second signaling moiety is sufficient to minimize, suppress, or prevent the first signaling moiety from emitting a detectable signal. When the DNA binding protein is present and binds to the recognition duplex of the probe, the internal hybridization of the probe is disrupted (e.g., the double stem-loop conformation of the probe is disrupted). Disruption of the internal hybridization allows the end of the nucleotide chain to which the first signaling moiety is attached to move to a distance further away from the second signaling moiety. Under conditions in the presence of the DNA binding protein, the distance the first signaling moiety moves away from the second signaling moiety is sufficient to allow the first signaling moiety to emit a detectable signal.

As described above, in the absence of binding of the DNA binding protein to the recognition duplex, the probe may be in a double stem-loop configuration. In these cases, the probe may adopt a conformation where the first signaling moiety is positioned adjacent the second signaling moiety, such that the probe does not produce a detectable signal. For example, the first signaling moiety may be a fluorophore and the second signaling moiety may be a quencher. In these instances, under conditions in the absence of the DNA binding protein, the distance the fluorophore is held from the quencher is sufficient to minimize, suppress, or prevent the fluorophore from emitting a detectable signal. When the DNA binding protein is present and binds to the recognition duplex of the probe, a conformational change in the probe is produced such that the fluorophore is able to move to a distance further away from the quencher. Under conditions in the presence of the DNA binding protein, the distance the fluorophore moves away from the quencher is sufficient to allow the fluorophore to emit a detectable signal.

DNA binding proteins that may be detected using the oligonucleotide probes may include, but are not limited to, proteins or peptides that specifically bind to DNA, such as transcription factors (e.g., TATA binding protein (TBP), Myc-Max, NF-KB, etc.), and the like.

Figure 11:
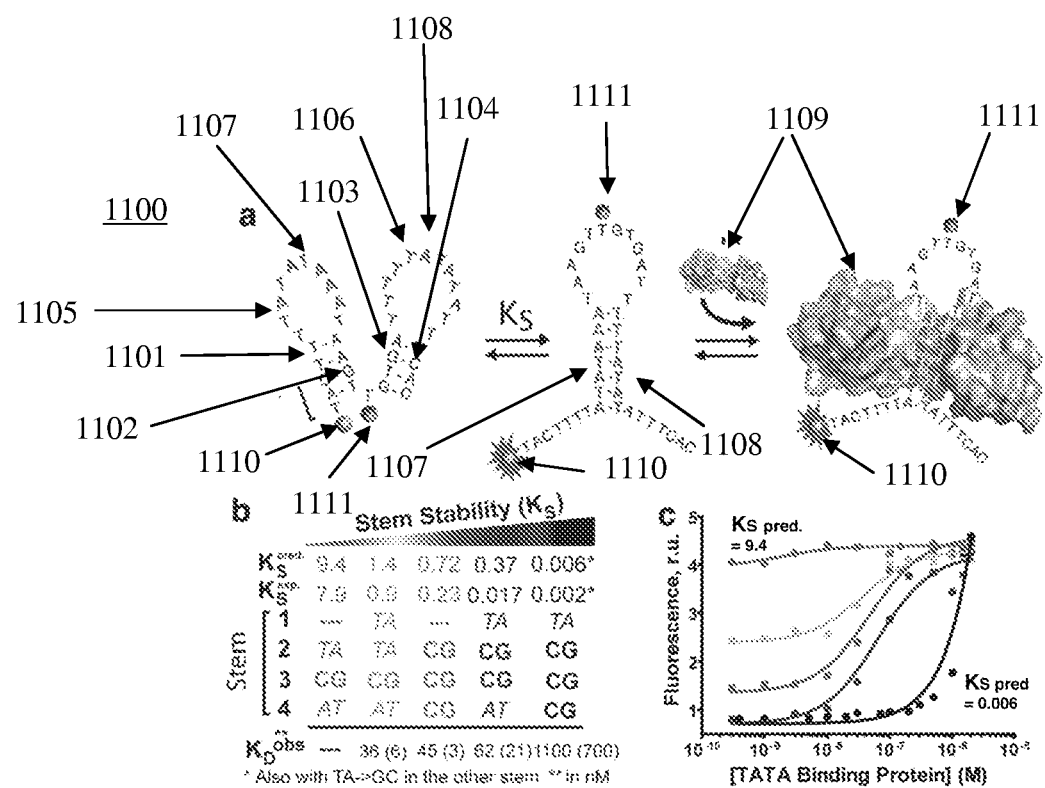
FIG. 11(a) shows a unimolecular oligonucleotide probe for detecting a DNA binding protein, according to embodiments of the present disclosure. The fluorescent signaling moieties used were FAM-6 for the fluorophore and BHQ-1 for the quencher.
FIG. 11(b) shows a chart of probe variants displaying various switching equilibrium constants, $K_S$, and dissociation constants, $K_D$, for TATA Binding Protein, according to embodiments of the present disclosure.
FIG. 11(c) shows a graph of fluorescence of these different variants vs. the concentration of a TBP target, according to embodiments of the present disclosure.

An example of an oligonucleotide probe 1100 for detecting a DNA binding protein is depicted in FIG. 11. An aspect of the oligonucleotide probe of FIG. 11 is that the probe has a double stem-loop structure formed by intramolecular hybridization of a single-stranded oligonucleotide. This stem-loop structure is formed through intramolecular hybridization between a first hybridization sequence 1101 and a second hybridization sequence 1102 to form a first duplex, and intramolecular hybridization between a third hybridization sequence 1103 and a fourth hybridization sequence 1104 to form a second duplex. First hybridization sequence 1101 and second hybridization sequence 1102 are separated by a first loop structure 1105 formed by the oligonucleotide sequence between first hybridization sequence 1101 and second hybridization sequence 1102. Third hybridization sequence 1103 and fourth hybridization sequence 1104 are separated by a second loop structure 1106 formed by the oligonucleotide sequence between third hybridization sequence 1103 and fourth hybridization sequence 1104.

In the absence of target binding to the probe, the probe may adopt a double stem-loop conformation that includes formation of the first and second duplexes as described above. The probe also includes a first recognition sequence 1107 and a second recognition sequence 1108. The first recognition sequence 1107 is formed by a portion of the first loop structure 1105, and the second recognition sequence 1108 is formed by a portion of the second loop structure 1106. The first recognition sequence 1107 and the second recognition sequence 1108 are complementary sequences that may hybridize to each other to form a recognition duplex. The conformation of the probe is in equilibrium between formation of the double stem-loop conformation and formation of the recognition duplex. In the absence of target 1109 binding to the probe 1100, the probe 1100 favors formation of the double stem-loop configuration, where the first recognition sequence 1107 is not hybridized to the second recognition sequence 1108. In the presence of target 1109, the equilibrium may be shifted towards the formation of the recognition duplex by target 1109 binding to the recognition duplex.

The oligonucleotide probe 1100 further includes a fluorophore 1110 and a quencher 1111. In FIG. 11, the fluorophore 1110 is coupled to one end of the oligonucleotide strand of the probe and the quencher 1111 is coupled to an internal site of the oligonucleotide strand of the probe. As described herein, the fluorophore may be coupled to the oligonucleotide strand of the probe at an internal site, and the quencher may be coupled to one end of the oligonucleotide strand of the probe. As shown in FIG. 11(a), in the absence of target 1109 binding to the recognition duplex, the internal hybridization between the first and second hybridization sequences (1101 and 1102) and the internal hybridization between the third and fourth hybridization sequences (1103 and 1104) positions the fluorophore 1110 adjacent the quencher 1111 such that the quencher 1111 substantially suppresses detectable emissions from the fluorophore 1110 (see also FIGS. 12 and 13). As shown in FIG. 11(a), binding of the target 1109 (e.g., a DNA binding protein, such as a transcription factor) to the recognition duplex causes a conformational change in the probe 1100 that positions the fluorophore 1110 at a distance away from the quencher 1111, such that the fluorophore 1110 produces a detectable signal (see also FIGS. 12 and 13).

In certain embodiments, the probe is configured to have switching thermodynamics (or equilibrium constant, $K_S$) between the non-bound state (e.g., double-stem-loop structure) and the target bound state (e.g., single stem-loop structure) where the equilibrium is shifted to the non-bound state (e.g., double-stem-loop structure) in absence of target binding (see FIG. 11(*a*)), without over-stabilizing this structure. Over-stabilization of the double-stem-loop may lead to a reduction of the affinity of the probe for the target (see FIGS. 11(*b*) and 11(*c*)). FIGS. 11(*b*) and 11(*c*) present different variants of probes with various switching thermodynamics that display various gain and affinity for the target. In certain embodiments, the $K_S$ ranges from 0.001 to 10, such as from 0.01 to 5, including from 0.1 to 2, or from 0.1 to 1.

Probes Configured to Produce Other Types of Signals Upon Target Binding

In certain embodiments, the probe is configured to produce a signal change through different signal output mechanisms. In some cases, the probe includes two target binding moieties, such as a first target binding moiety and a second target binding moiety. Various signaling moieties may be used, where the first and second signaling moieties produce a detectable signal change upon target binding. The detectable change in signal includes, but is not limited to, a detectable signal decrease when a target specifically binds to the probe to form a target-probe hybrid, or a detectable increase in signal when a target specifically binds to the probe to form a target-probe hybrid. In certain embodiments, the first signaling moiety is a detectable reporter and the second signaling moiety is a detector configured to detect the reporter. Suitable reporters may include reporters that are detectable by the detector, such as, but not limited to, electrochemical reporters, magnetic reporters, and the like.

In certain embodiments, the first signaling moiety is an electrochemical reporter and the second signaling moiety is an electrode. In some cases, the use of an electrochemical reporter and an electrode as the signaling moieties may facilitate target detection directly in whole blood or other complex clinical, food and environmental samples. In certain instances, under conditions in the absence of target, the distance the electrochemical reporter is held from the electrode is sufficient to produce a detectable signal (see e.g., FIG. 8). In certain embodiments, when target is present and binds to both the target binding moieties of the probe, the internal hybridization of the probe is disrupted such that the electrochemical reporter is able to move to a distance further away from the electrode (see e.g., FIG. 8). Under these conditions, in the presence of target binding, the distance the electrochemical reporter moves away from the electrode is sufficient to produce a detectable change in the signal, such as a detectable decrease in the signal (see e.g., FIG. 8). In other embodiments, under conditions in the absence of target, the electrochemical reporter is held a distance away from the electrode, such that a detectable signal is not produced or a low detectable signal is produced (see e.g., FIG. 14). In certain embodiments, when target is present and binds to the target binding moiety of the probe, the electrochemical reporter is positioned adjacent to the electrode (see e.g., FIG. 14). Under these conditions, in the presence of target binding, positioning the electrochemical reporter adjacent to the electrode is sufficient to produce a detectable change in the signal, such as a detectable increase in the signal (see e.g., FIG. 14).

In some instances, the probe may be attached to the surface of a substrate. As described above, the first signaling moiety may be an electrochemical reporter and the second signaling moiety may be an electrode. As such, the probe may be attached to the surface of the electrode. The probe may be attached by any convenient attachment method suitable for attachment of the oligonucleotide probe to the surface of the substrate. For example, the probe may include modified nucleotides configured to be attached to the surface of the substrate, such as, but not limited to nucleotides modified to include a thiol group. The probe may be attached to the surface of the substrate directly, such as by covalent attachment of the probe to the surface of the substrate, or indirectly, such as through a linker moiety or by affinity binding (e.g., through streptavidin-avidin complex formation, and the like).

Figure 8:
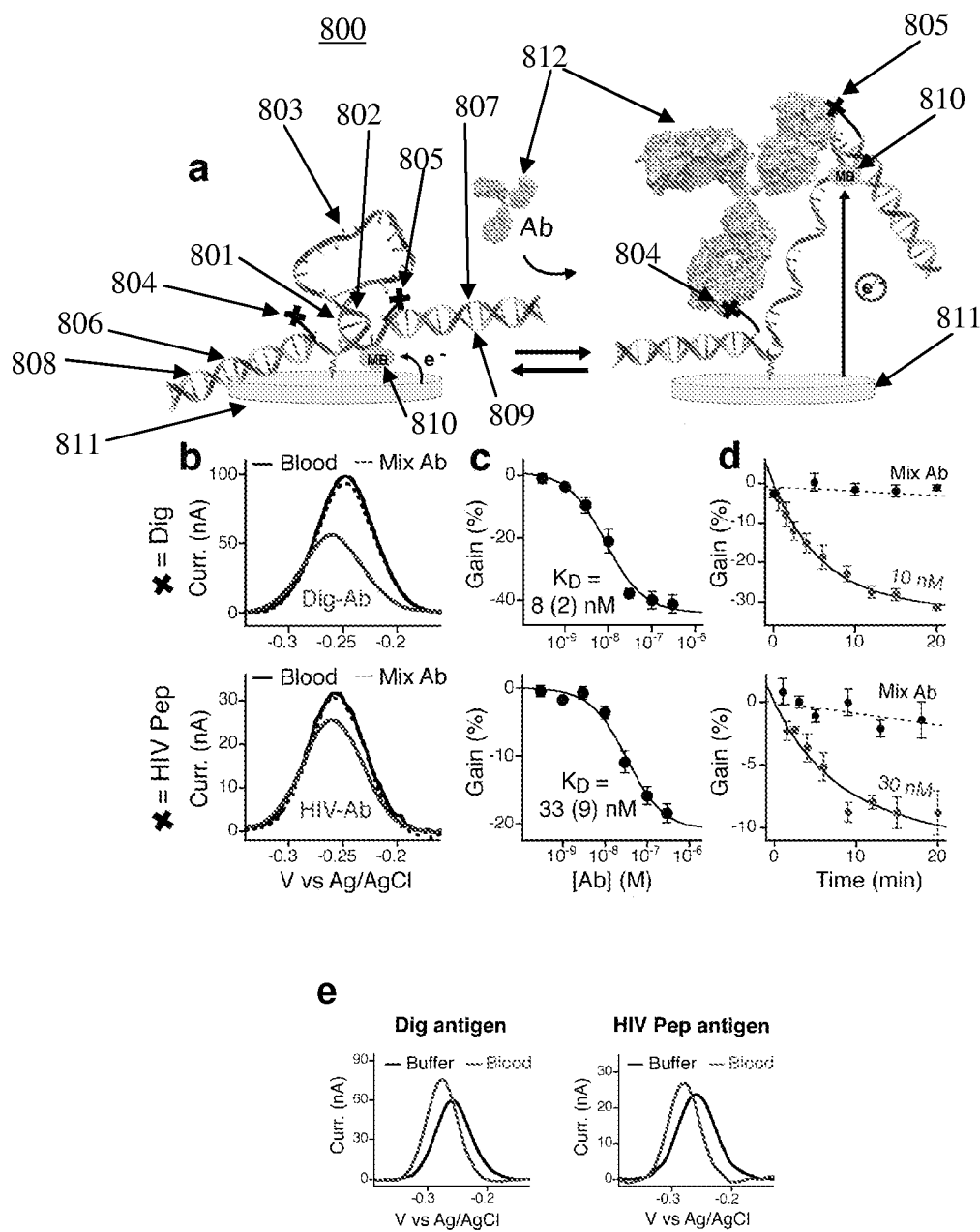
FIG. 8(a) shows a modular unimolecular oligonucleotide probe that uses an electrochemical reporter (e.g., methylene blue) and an electrode as the two signaling moieties, according to embodiments of the present disclosure.
FIG. 8(b) shows graphs of square wave voltammograms for anti-Dig antibody and anti-HIV antibody probes, according to embodiments of the present disclosure (results were obtained in 80% whole blood using a probe stem with 1MM and 2GC and 2AT).
FIG. 8(c) shows graphs of current signal vs. target concentration for anti-Dig antibody and anti-HIV antibody probes, according to embodiments of the present disclosure (results were obtained in 80% whole blood).
FIG. 8(d) shows graphs of current signal vs. time for anti-Dig antibody and anti-HIV antibody probes, according to embodiments of the present disclosure.
FIG. 8(e) shows graphs of square wave voltammograms for anti-Dig antibody and anti-HIV antibody probes in buffer and 80% whole blood, according to embodiments of the present disclosure.

An example of an oligonucleotide probe 800 configured to produce a detectable electrochemical signal change upon target binding is depicted in FIG. 8. An aspect of the oligonucleotide probe of FIG. 8 is that the probe has a stem-loop structure formed by intramolecular hybridization of a single-stranded oligonucleotide. This stem-loop structure is formed through intramolecular hybridization between a first hybridization sequence 801 and a second hybridization sequence 802. Internal hybridization between first hybridization sequence 801 and second hybridization sequence 802 forms a duplex. First hybridization sequence 801 and second hybridization sequence 802 are separated by a loop structure 803 formed by the oligonucleotide sequence between first hybridization sequence 801 and second hybridization sequence 802.

The oligonucleotide probe also includes a first target binding moiety 804 and a second target binding moiety 805. The probe 800 also includes third hybridization sequence 806 and fourth hybridization sequence 807. The first target binding moiety 804 is attached to a fifth hybridization sequence 808, and the second target binding moiety 805 is attached to a sixth hybridization sequence 809. As depicted in FIG. 8(*a*), the first target binding moiety 804 and the second target binding moiety 805 are indirectly attached to the probe by hybridization between third hybridization sequence 806 and fifth hybridization sequence 808, and by hybridization between fourth hybridization sequence 807 and sixth hybridization sequence 809, respectively.

The oligonucleotide probe 800 further includes an electrochemical reporter 810 (e.g., methylene blue). The probe 800 is attached to an electrode 811. In FIG. 8, the electrochemical reporter 810 is coupled to the probe at an internal site. In addition, the probe is attached to the electrode 811 at an internal site. As described herein, the electrochemical reporter and/or the electrode may be coupled to the oligonucleotide strand of the probe at other sites, such as at or near the end of the oligonucleotide strand of the probe. As shown in FIG. 8(*a*), in the absence of target binding to the target binding moieties (804 and 805), the internal hybridization between the first and second hybridization sequences (801 and 802) positions the electrochemical reporter 810 adjacent the electrode 811 such that the probe produces a detectable signal (see FIGS. 8(*c*) and 8(*d*)). As shown in FIG. 8(*a*), binding of the target 812 (e.g., an antibody) to the first and second target binding moieties (804 and 805) causes a conformational change in the probe 800 that positions the electrochemical reporter 810 at a distance away from the electrode 811, such that the probe produces a detectable signal decrease (see FIGS. 8(*c*) and 8(*d*)).

Figure 10:
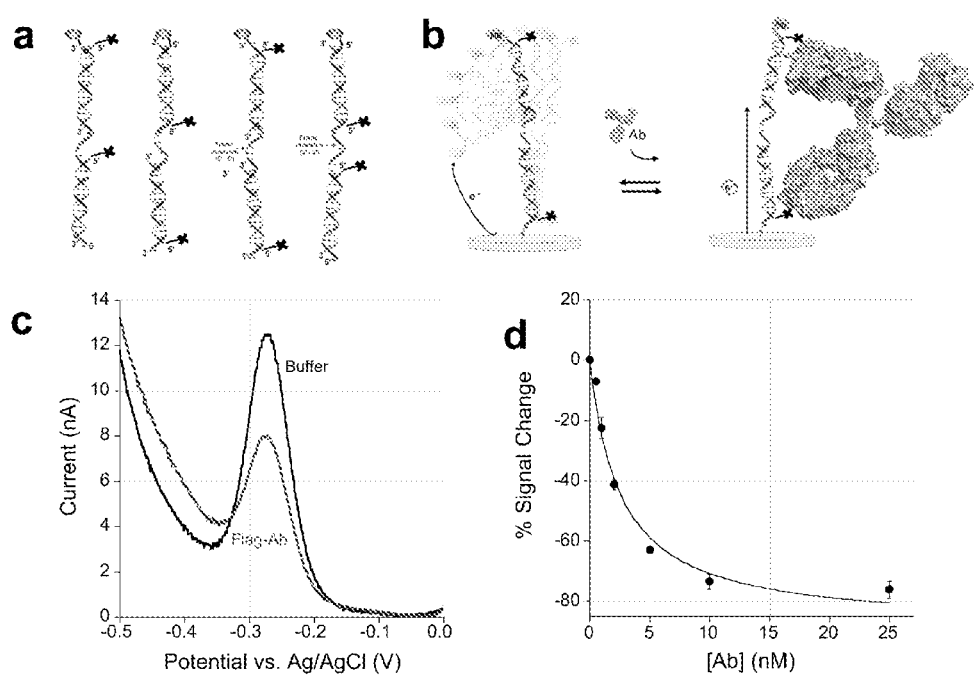
FIG. 10(a) shows a probe that works in absence of a stem region in which the target binding moieties can be positioned at various locations, according to embodiments of the present disclosure.
FIG. 10(b) shows a schematic of how target binding changes the distance between the two signaling moieties, according to embodiments of the present disclosure.
FIG. 10(c) shows graphs of square wave voltammograms for anti-Flag antibody probes, according to embodiments of the present disclosure.
FIG. 10(d) shows a graph of current signal vs. target concentration for anti-Flag antibody probes, according to embodiments of the present disclosure.

As described above, in the absence of target binding to the target binding moieties, the probe may also be in a flexible conformation (e.g., without a stem-loop structure) (FIG. 10(a)). In these cases, the first signaling moiety can transiently move into proximity with or bind to the second signaling moiety, such that the signal from these signaling moieties changes (FIG. 10 (b)). For example, the first signaling moiety may be an electrode and the second signaling moiety may be an electrochemical reporter. In these instances, under conditions in the absence of target, positioning the electrochemical reporter proximal to the electrode is sufficient to produce a detectable signal. When target is present and binds to the target binding moieties of the probe, the probe may be in a conformation where the electrochemical reporter is positioned such that does not approach the electrode as readily or as frequently. Under conditions in the presence of target binding, the distance the electrochemical reporter moves away from the electrode may produce a detectable current signal change (FIGS. 10(c) and 10(d)).

Figure 14:
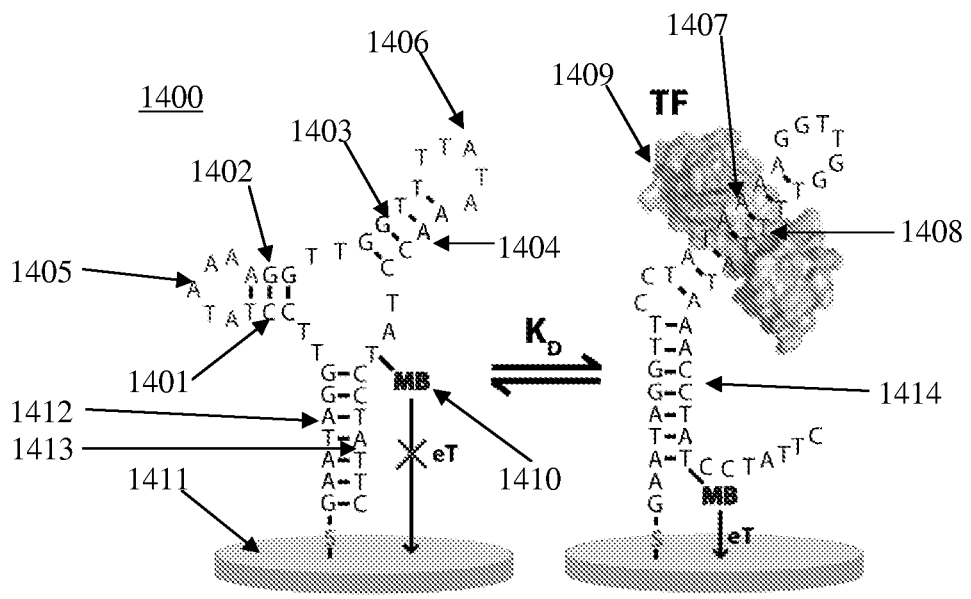
FIG. 14 (top) shows a unimolecular oligonucleotide probe for the detection of a DNA binding protein, that uses an electrochemical reporter (e.g., methylene blue) and an electrode as the two signaling moieties, according to embodiments of the present disclosure.
Figure 14:
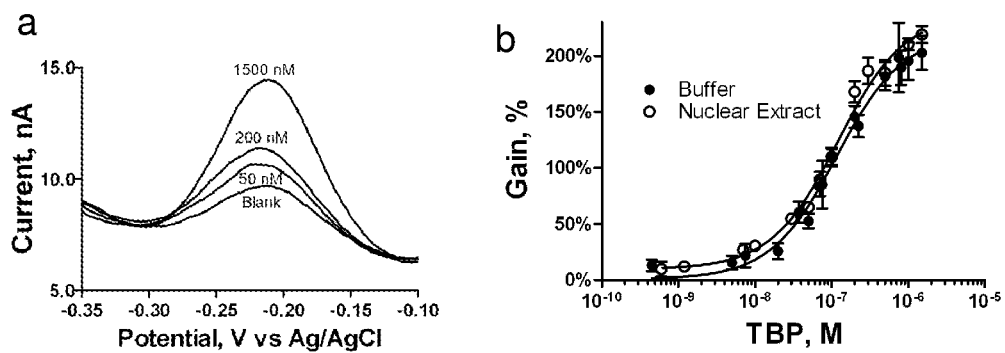

Different signal output mechanisms may be also applied for the detection and quantification of a DNA binding protein in a sample. An example of an oligonucleotide probe 1400 for detecting a DNA binding protein through electrochemical detection is depicted in FIG. 14 (top). The oligonucleotide probe 1400 of FIG. 14 has a double stem-loop structure formed by intramolecular hybridization of a single-stranded oligonucleotide. This double stem-loop structure is formed through intramolecular hybridization between a first hybridization sequence 1401 and a second hybridization sequence 1402 to form a first duplex, and intramolecular hybridization between a third hybridization sequence 1403 and a fourth hybridization sequence 1404 to form a second duplex. First hybridization sequence 1401 and second hybridization sequence 1402 are separated by a first loop structure 1405 formed by the oligonucleotide sequence between first hybridization sequence 1401 and second hybridization sequence 1402. Third hybridization sequence 1403 and fourth hybridization sequence 1404 are separated by a second loop structure 1406 formed by the oligonucleotide sequence between third hybridization sequence 1403 and fourth hybridization sequence 1404. In the absence of target binding to the probe, the probe may adopt a double stem-loop conformation that includes formation of the first and second duplexes as described above. The probe also includes a first recognition sequence 1407 and a second recognition sequence 1408. The first recognition sequence 1407 is formed by at least a portion of the first loop structure 1405, and the second recognition sequence 1408 is formed by at least a portion of the second loop structure 1406. The first recognition sequence 1407 and the second recognition sequence 1408 are complementary sequences that may hybridize to each other to form a recognition duplex. The conformation of the probe is in equilibrium between formation of the double stem-loop conformation and formation of the recognition duplex. In the absence of target 1409 binding to the probe 1400, the probe 1400 favors formation of the double stem-loop configuration, where the first recognition sequence 1407 is not hybridized to the second recognition sequence 1408. In the presence of target 1409, the equilibrium may be shifted towards the formation of the recognition duplex by target 1409 binding to the recognition duplex. The oligonucleotide probe 1400 further includes an electrochemical reporter 1410 (e.g., methylene blue). In FIG. 14 (top), the electrochemical reporter 1410 is coupled to the probe at an internal site. In addition, the probe is attached to the electrode 1411 at one end. As described herein, the electrochemical reporter and/or the electrode may be coupled to the oligonucleotide strand of the probe at other sites, such as at or near the end of the oligonucleotide strand of the probe. As shown in FIG. 14 (top), in the absence of target 1409 binding to the recognition duplex, the internal hybridization between the first and second hybridization sequences (1401 and 1402) and the internal hybridization between the third and fourth hybridization sequences (1403 and 1104) positions the electrochemical reporter 1410 at a distance away from the electrode 1411, such that the electrochemical reporter 1410 shows a decreased electron transfer rate (e.g., a low or not significantly detectable electrochemical signal) (see FIG. 14 (top)). As shown in FIG. 14 (top), binding of the target 1409 (e.g., a DNA binding protein, such as a transcription factor, TF) to the recognition duplex causes a conformational change in the probe 1400 that positions the electrochemical reporter 1410 adjacent the electrode 1411, such that the electrochemical reporter 1410 produces a greater detectable electrochemical signal compared to the signal in the absence of target 1409 (see FIGS. 14(a) and 14(b)). The probe 1400 may also include a fifth hybridization sequence 1412 and a sixth hybridization sequence 1413 configured to hybridize to each other to form a third duplex. The third duplex may be adjacent the electrochemical reporter 1410. In the absence of target 1409 binding to the recognition duplex, the fifth hybridization sequence 1412 and the sixth hybridization sequence 1413 are hybridized and position the electrochemical reporter 1410 at a distance away from the electrode 1411 as described above. When target 1409 is bound to the recognition duplex, a fourth duplex 1414 may be formed adjacent the electrochemical reporter 1410 that positions the electrochemical reporter adjacent the electrode 1411 as described above.

Methods

Detection of Targets Using Oligonucleotide Probe-Based Detectors

Provided are methods for detecting the presence of a target in a sample using unimolecular oligonucleotide probe-based detectors. Aspects of the methods include contacting a sample suspected of containing a target with a probe of the present disclosure under conditions that allow target that may be present in the sample to specifically bind to the target binding moieties of the probe. Binding of the target to the probe causes a conformational change in the probe, which in turn produces a detectable signal or a detectable change in a signal. For example, binding of the target to the probe may position a fluorophore at a distance away from a quencher sufficient to allow a signal of the fluorophore to be detectable. In other embodiments, binding of the target to the probe may position a reporter moiety at a distance away from a detector sufficient to allow a change in a signal from the detector to be detectable.

The detectable signal or the detectable change in signal may be compared to control readouts from control samples that do not contain target or to results from samples that contain targets that do not specifically bind to the target binding moieties of the probe (e.g., negative controls). In other embodiments, the signal detected by the detector may be optionally compared to control readouts for control samples that contain target or a known amount of target (e.g., positive controls). Numerous alternative controls may be performed individually or in combination, as is known to those of skill in the art. For example, the control may be to challenge the probe with a surrogate solution absent the sample, and thus lacking target. Alternatively, the control may be a solution containing a target derivative that may have similarity to the actual target, but is normally not recognized and specifically bound by the probe under specific binding or "stringent" conditions.

Suitable samples include bodily fluids (e.g., blood, urine, interstitial fluid, lachrymal fluid, sweat, saliva, and the like), water, cell extracts, cell suspensions, secretions, solvents, and other aqueous and organic liquid solutions, suspension or emulsions capable of including the target of the probe of the detector. Samples may also include complex samples, such as, but not limited to, whole blood, crude nuclear extracts, and the like. In certain embodiments, the probes of the present disclosure are oligonucleotides that include target binding moieties, such as antigens, that specifically bind to target antibodies. In other embodiments, the probes are oligonucleotides that include complementary intramolecular hybridization sequences that hybridize to form a recognition duplex, which is specifically bound by a target DNA binding protein. In certain embodiments, the probes of the present disclosure are oligonucleotides that include target binding moieties, such as polypeptides, that specifically bind to target macromolecules. In certain embodiments, the probes of the present disclosure are oligonucleotides that include target binding moieties, such as aptamers, that specifically bind to target macromolecules.

Reaction Conditions and Detection Methods

The methods disclosed herein may be carried out in any reaction medium that allows specific binding between probe and, if present, target as defined herein. In cases where the sample contains target that specifically binds to the target binding moieties of the probe, specific binding between the target binding moieties of the probe and the target is favored over intramolecular hybridization between the internal hybridization sequences of the probe. In cases where the sample contains targets that do not specifically bind to the target binding moieties of the probe, intramolecular hybridization between the internal hybridization sequences of the probe is favored over binding between the probe and mismatched target.

Binding reactions involving the probes disclosed herein may be carried out in the presence of agents and additives that promote the desired specific binding, diminish nonspecific background interactions, inhibit the growth of microorganisms, or increase the stability of the probe and/or target. Binding reactions of the disclosure may be carried out at ambient temperature, although any temperature in the range allowing specific binding may be used. For instance in some embodiments, the temperature range is from 5° C. to 45° C., such as from 10° C. to 40° C., or from 20° C. to 30° C. In addition, in some embodiments, the pH of the binding reaction medium is about physiological pH. For example, the pH may range from 4 to 10, such as 5 to 9, including 6 to 8. In certain cases, the pH may be 7. For convenience, reaction conditions may be chosen to allow specific binding to occur as rapidly as possible. Binding times as short as seconds (e.g., 1 to 60 seconds), or minutes (e.g. 1 to 30 minutes) may be employed. By way of example, times of 1 to 60 seconds, such as 10 to 60 seconds, including 20 to 60 seconds may be used. In other embodiments, times of 1 to 30 minutes, such as 5 to 20 minutes, including 10 to 20 minutes may be used.

Multiplexing

In certain embodiments, the methods may include multiplex detection of targets. The terms "multiplex" or "multiplexing" as used herein refer to using multiple distinct signaling moieties, such that a single assay may be used to detect the presence of different targets in a single sample.

For example, in embodiments that include fluorescent signaling moieties, the system may include multiple fluorescently distinct fluorophores, such that a single assay may include multiple probes each with different fluorophores. Fluorophores of these embodiments emit detectable signals at different wavelengths. Multiplexing facilitates the detection of different targets of interest within a single sample (e.g., targets that specifically bind to different target binding moieties). In these embodiments, a mixture of differentially labeled probes (e.g., a first probe with a first fluorophore and a second probe with a second fluorophore) may be contacted with a sample that includes one or more different targets of interest. For example, a first target may bind to a first target binding moiety and a second target binding moiety of a first probe, as described above. A second target may bind to a third target binding moiety and a fourth target binding moiety of a second probe. Upon binding of the first target to the first and second target binding moieties of the first probe, a conformational change is induced in the first probe such that the first probe produces a detectable first signal. In addition, upon binding of the second target to the third and fourth target binding moieties of the second probe, a conformational change is induced in the second probe such that the second probe produces a second detectable signal that is distinct from the first signal. Both the first signal and the second signal may be detected, thus indicating the presence (or absence) of the first target and the second target in the sample. In certain embodiments, multiplexing may be used in reactions that include unbound probes in solution. In other embodiments, multiplexing may be used in systems comprising arrays or addressable arrays of probes attached to a substrate surface.

Similarly, multiplexing may be applied to embodiments that include electrochemical signaling moieties. In these embodiments, two or more different probes may be contacted with a sample that includes one or more different targets of interest. For example, the system may include a first probe that includes a first and a second target binding moieties and a second probe with a third and a fourth target binding moieties. The first and the second target binding moieties may be different from the third and the fourth target binding moieties, such that a first target binds to the first and second target binding moieties and a second target binds to the third and fourth target binding moieties. Upon binding of the first target to the first and second target binding moieties of the first probe, a conformational change is induced in the first probe such that the first probe produces a detectable change in a first signal. In addition, upon binding of the second target to the third and fourth target binding moieties of the second probe, a conformational change is induced in the second probe such that the second probe produces a detectable change in a second signal that is distinct from the first signal. The changes in the first and second signals may be detected, thus indicating the presence (or absence) of the first target and the second target in the sample.

Utility

The subject systems and methods find use in a variety of different applications where determination of the presence or absence, and/or quantification of one or more targets in a sample is desired. In certain embodiments, the methods are directed to the detection of proteins, carbohydrates, nucleic acids, lipids, peptides, enzymes or other biomolecules in a sample. Samples may include, but are not limited to, blood, plasma, serum, or other bodily fluids or excretions, such as but not limited to, urine, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like.

The presence or absence of a target in a sample or significant changes in the concentration of a target over time can be used to diagnose disease risk, presence of disease in an individual, or to tailor treatments for the disease in an individual. For example, the presence of a particular target or panel of targets may influence the choices of drug treatment or administration regimes given to an individual. In evaluating potential drug therapies, the presence, absence, or concentration of a target may be used as a surrogate for a natural endpoint such as survival or irreversible morbidity. If a treatment alters the target, which has a direct connection to improved health, the target can serve as a surrogate endpoint for evaluating the clinical benefit of a particular treatment or administration regime. Thus, personalized diagnosis and treatment based on the particular target or panel of targets detected in an individual are facilitated by the subject systems and methods. Furthermore, the early detection of targets associated with diseases is facilitated by the high sensitivity of the subject systems and methods, as described above. Due to the multiplex capability of detecting multiple targets in a single assay, combined with selectivity, sensitivity and ease of use, the presently disclosed systems and methods find use in quantitative, point-of-care or near-patient bio-molecular assays.

The subject systems and methods find use in diagnostic assays, such as, but not limited to, the following: detecting and/or quantifying targets, as described above; screening assays, where samples are tested at regular intervals for asymptomatic subjects; prognostic assays, where the presence and or quantity of a target is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject systems and methods may facilitate an increase in the throughput for screening a plurality of samples in a minimum amount of time.

In certain embodiments, the subject systems and methods find use in detecting antibodies in a sample. In some cases, the subject systems and methods may be used to detect the presence or absence of particular antibodies, as well as an increase or decrease in the concentration of particular antibodies in a sample.

In certain embodiments, the subject systems and methods find use in detecting DNA binding proteins, such as transcription factors. The subject systems and methods may be used to detect the presence or absence of particular DNA binding proteins, as well as an increase or decrease in the concentration of particular DNA binding proteins in a sample. For example, given their nanoscale size and their ability to provide a readout signal without the need of additional reagents, transcription factor probes could be transferred into a cell nucleus (e.g., by transfection, coupled with an appended nuclear localization peptide) allowing fluorescent microscopy to track the concentration of active transcription factor during cell growth or upon administration of a drug compound. Resonance energy transfer-based signaling fluorophores may be used, as the ratiometric nature of these types of fluorophores corrects for varying probe concentrations. Transcription factor probes may also find use in drug screening assays, for example by ensuring that the optical signal changes obtained due to the presence of a specific drug are specifically linked to the DNA-protein target interaction and not solely attributable to off-target drug interactions. Transcription factor probes may also be amenable to other signaling mechanisms, such as, but not limited to, electrochemical signaling moieties as described above, which may facilitate use of these probes in complex samples.

Kits

Also provided are kits that find use in practicing the subject methods, as described above. For example, kits and systems for practicing the subject methods may include one or more systems of the present disclosure, which may include one or more probes. As such, in certain embodiments the kits may include a solution or suspension of the probes in an aqueous or other compatible solution. The one or more probes may be provided in separate containers with each container including a single type of probe, or may be provided in a container that includes a mixture of two or more types of probes. In other embodiments, the kits may include one or more probes immobilized on the surface of a substrate forming an addressable array of probes as described above.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Examples

Fluorescent Probes
  Fluorescent Probes for Antibody Detection
  The first probe was tested by using a DNA sequence that includes a stem-loop with a relatively weak stem-loop conformation with switching thermodynamics ($K_S$) of about 1. A stable, GC-rich stem was successively destabilizing by 1 kcal/mol increments until a stem sequence was identified that favored the stem-loop conformation without over stabilizing the stem-loop conformation (see FIG. 1(b), construct 1MM with one "T-T" miss match in the middle of the stem) at room temperature, thus facilitating the binding-induced opening of the stem-loop structure of the probe. Over-stabilization of the probe may facilitate undesired binding of two molecules of the target to a single probe.

Figure 2:
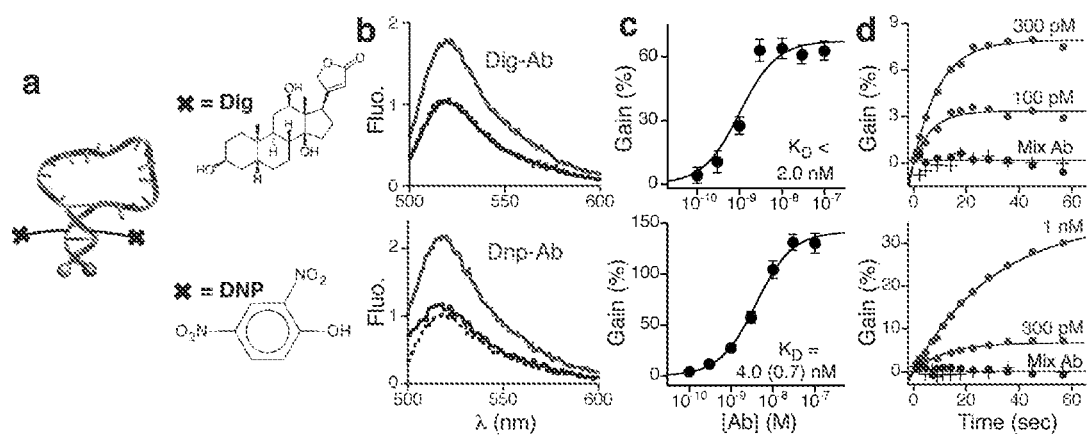
FIG. 2(a) shows a unimolecular oligonucleotide probe configured to produce a detectable fluorescent signal upon target binding, according to embodiments of the present disclosure. The fluorescent signaling moieties are FAM-6 for the fluorophore and BHQ-1 for the quencher.
FIG. 2(b) shows graphs of fluorescence vs. wavelength for anti-Dig antibody and anti-DNP antibody probes according to embodiments of the present disclosure. The stem sequence used was 1MM (see FIG. 1(b)).
FIG. 2(c) shows graphs of signal vs. target concentration for anti-Dig antibody and anti-DNP antibody probes according to embodiments of the present disclosure.
FIG. 2(d) shows graphs of signal vs. time for anti-Dig antibody and anti-DNP antibody probes according to embodiments of the present disclosure.

A pair of fluorescent antibody probes employing the haptens 2,4-dinitrophenol (DNP) and digoxigenin (Dig) as target binding moieties, and thus targeting anti-Dig and anti-DNP antibodies respectively were prepared (FIG. 2). The target binding moieties were covalently attached to the stems of the probe using two different strategies: Dig was attached via amine linkers on the C-5 positions of the two thymines in the middle of the double-stranded stem, and DNP was inserted within the stem via the introduction of additional phosphodiester bonds (see Material and Methods below). To facilitate antibody-driven conformational changes in the probe, the two strands of the stem were connected via an 18-base loop that spanned the 12 nm distance between the two antigen binding sites present on the target antibody. 6-carboxyfluorescein (6 FAM) and Black Hole Quencher 1 (BHQ-1) were attached to the 5' and 3' termini of the stem to produce a detectable fluorescent signal upon opening of the stem-loop structure of the probe.

The anti-Dig and anti-DNP antibody probes produced 65% and 130% increases in fluorescence, respectively, at saturating target concentrations (FIG. 2(b)). Both probes responded to their respective target antibodies at 30 nM (FIG. 2(b)), and no increase in fluorescence was observed when the two antibodies were interchanged (FIG. 2(b), dotted line). The two probes displayed low-nanomolar affinities and equilibration times of one minute or less (FIG. 2(c)), and achieved detection limits of 100 pM and 300 pM (e.g., 15 and 45 ng/ml) in less than one minute for anti-Dig and anti-DNP antibody probes, respectively (FIG. 2(d)). The probes were specific for their respective target antibodies as no statistically significant increase in fluorescence was observed when either probe was incubated with 30 nM of the other's target (FIG. 2(d), black dots) or when challenged with a 1000-fold higher concentration (e.g., 3 µM) of non-specific pooled human antibodies (FIG. 2(d)). The titrations and kinetic traces shown in FIG. 2 represent the average of at least three independent measurements, with error bars reflecting the average absolute deviation.

Figure 3:
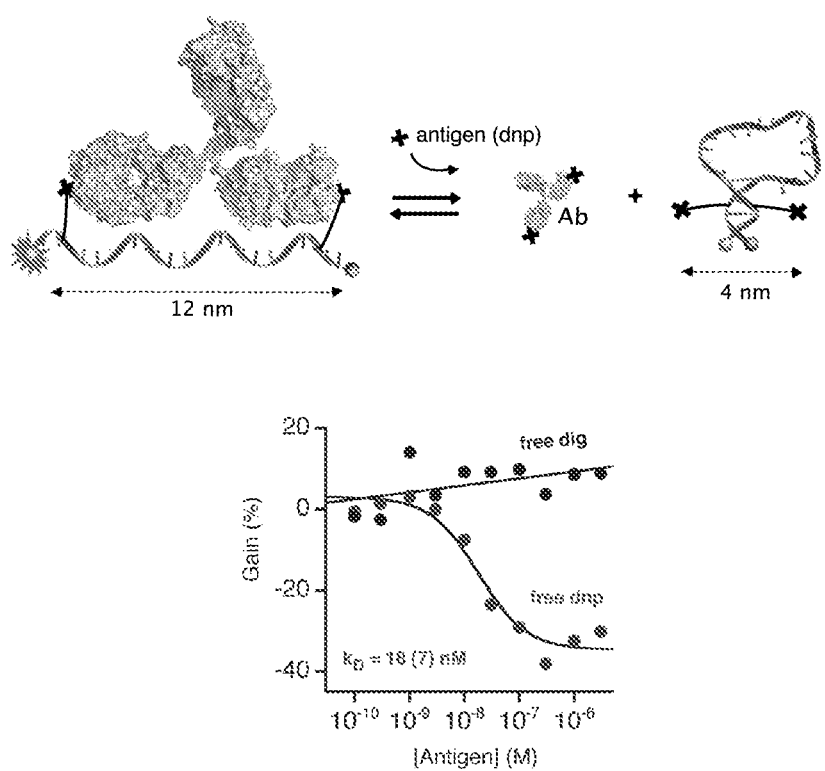
FIG. 3 shows the detection of a target (e.g., the antigen DNP) in a sample using the anti-DNP antibody probe in a competition assay, according to embodiments of the present disclosure.

Probes were also tested in a competitive assay format in order to detect small molecules such as DNP. The DNP-modified probe (10 nM) loaded with a minimal concentration of anti-DNP antibodies (10 nM) was used to detect the presence of free DNP but not free Dig (FIG. 3). An anti-DNP antibody probe was first bound to its specific anti-DNP antibody. In the presence of free DNP in the sample (and not free Dig), the antibody bound to the free DNP and was released from the probe, thus leading to a decrease in fluorescence signal. The apparent inhibition constant ($IC_{50\%}$) of the free DNP (or apparent affinity of the probe-bound antibody for free DNP) was significantly higher (4-fold) than the dissociation constant of the antibody-probe complex itself (see FIG. 2(c), bottom), which reflected the cooperative binding of a single antibody to the two antigens on the probe. In FIG. 3, the "free" DNP and "free" Dig were covalently linked to small poly-thymine constructs (TTTT-antigen-TTT) in order to insure that the increased affinity observed between the antibody and its probe was not attributable to the presence of the chemical bond linking the antigen to the probe.

Another embodiment of the probe is shown in FIG. 4, which depicts a modular unimolecular probe according to embodiments of the present disclosure. In this modular probe, the target binding moieties were indirectly attached to the probe by hybridization to the probe of two copies of a 17-base DNA strand modified with the target binding moiety (FIG. 4(a)). The stem-loop contained a frame inversion near one end to allow for symmetrical labeling of two copies of the same modified hybridization sequence. This may facilitate a reduction in fabrication cost and complexity. The modular probes were made using both Dig and an 11-residue polypeptide epitope from the HIV-1 protein gp41 as target binding moieties (FIG. 4). Specific detection of anti-Dig antibodies (FIG. 4(b), top) and anti-HIV antibodies (FIG. 4(b), bottom) were tested. Experimental results indicated that their gain, affinity, specificity and kinetics (FIGS. 4(b) and (c)) compare closely to those of the non-modular probes described above. The anti-HIV antibody probe, for example, achieved a 300 pM detection limit (e.g., 45 ng/ml), a 12 second response time constant, and a dissociation constant of 4±2 nM.

Figure 5:
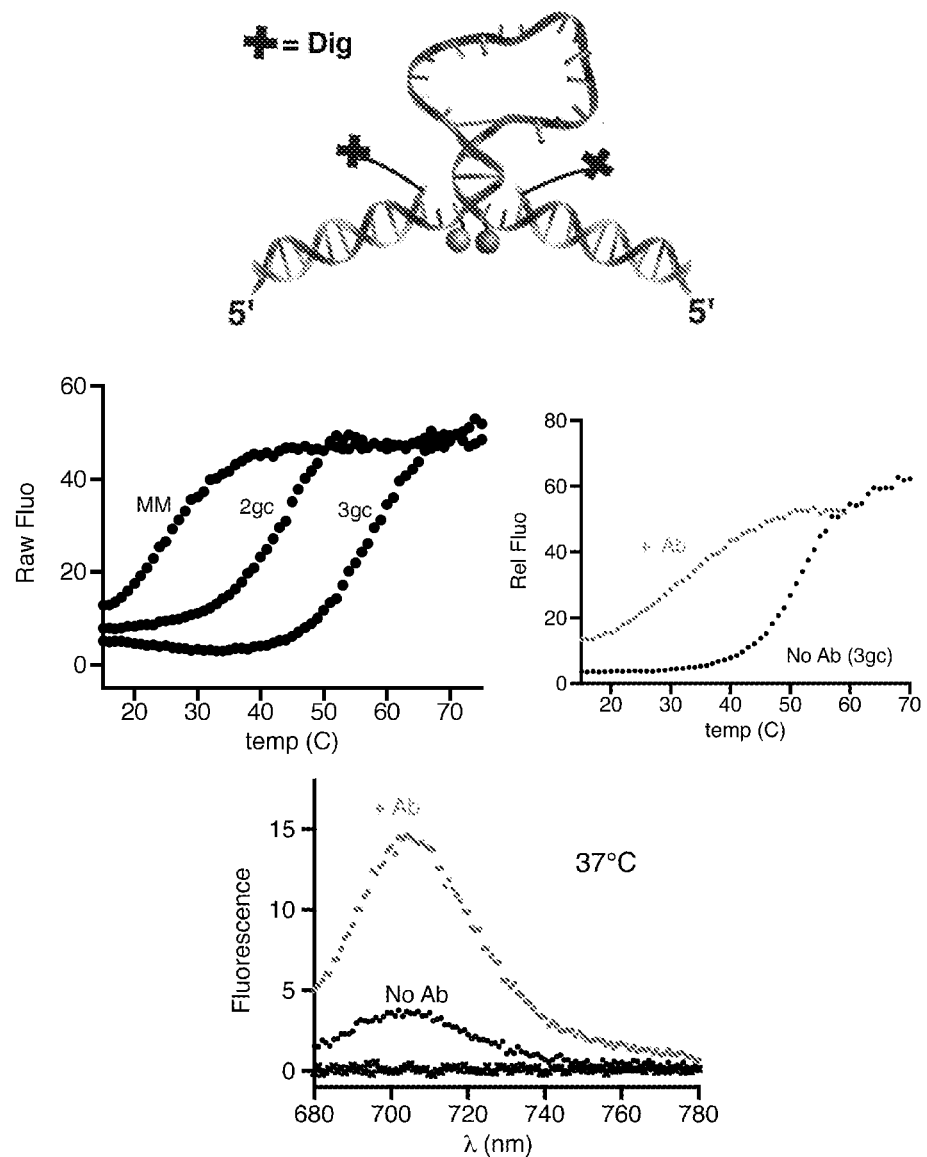
FIG. 5 shows a modular oligonucleotide probe configured to produce a high detectable fluorescent signal upon target binding, according to embodiments of the present disclosure.

Modular unimolecular probes were configured to produce a high detectable fluorescent signal upon target binding (see FIG. 5). The optimal gain of the modular switch at 37° C. was obtained when using a 3GC stem (e.g., a stem containing five Watson-Crick base-pairs with 3 GC and 2 AT base pairs). This stem stability facilitated a minimization in the background fluorescence in the absence of antibody, while still allowing stem opening upon binding to the antibody.

Figure 6:
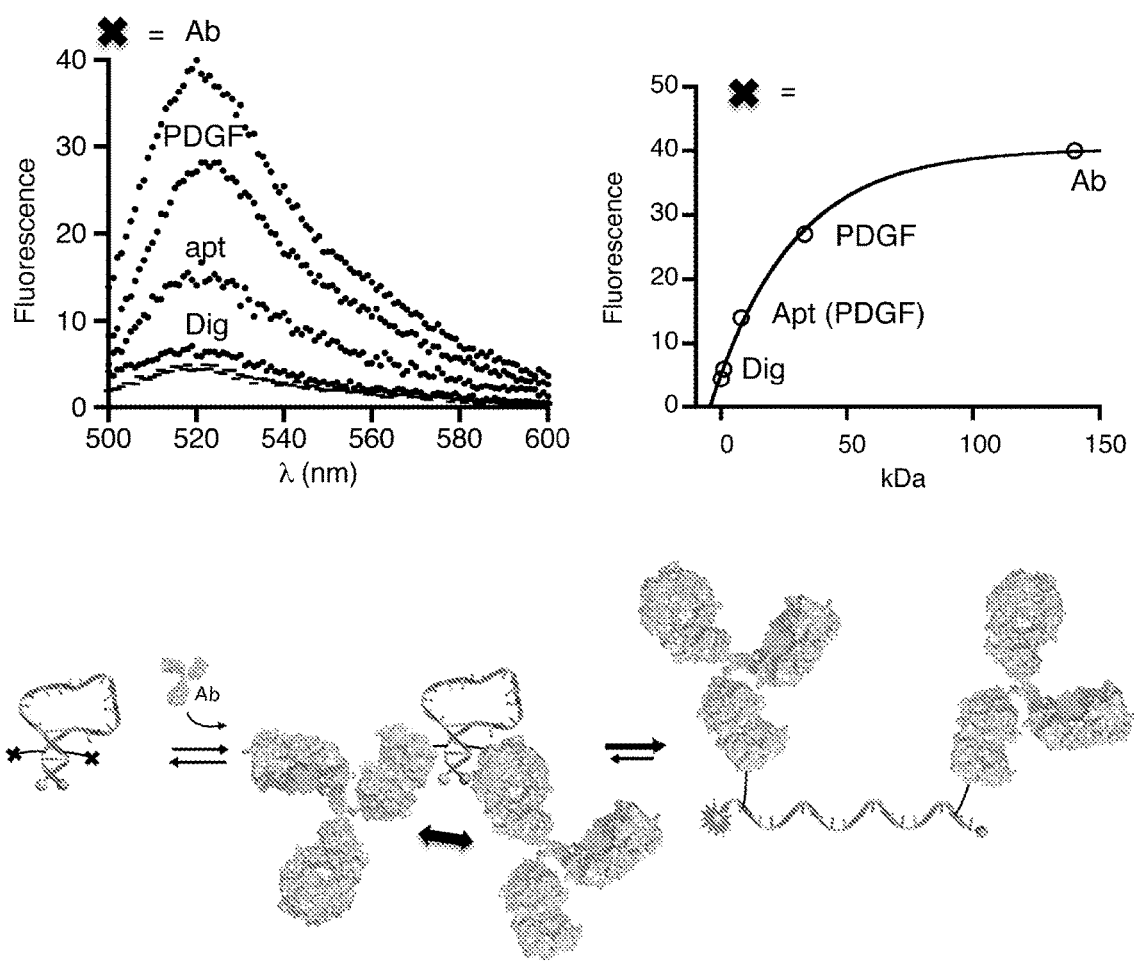
FIG. 6 (top) shows graphs of fluorescence vs. wavelength (nm) and fluorescence vs. target size (kDa) for modular oligonucleotide probes, according to embodiments of the present disclosure.

Probes were also tested for the detection of targets of different sizes (see FIG. 6 (top)). The fluorescence signal of the modular oligonucleotide probe was correlated to the size of the binding moieties (X) and the target bound to them. FIG. 6 (bottom) shows a schematic of the signaling of the modular probe (e.g., the probe stem opening) in the presence of two targets binding to a single probe. In some instances, the probe stem opening may be attributable to a steric-hindrance mechanism linked to the binding of two targets to a single probe (e.g., one target bound at each binding moiety, X). In certain cases, binding of one target to each binding moiety facilitated detection of non-bidentate targets (for example PDGF), e.g., a target that only contains one binding site.

Figure 7:
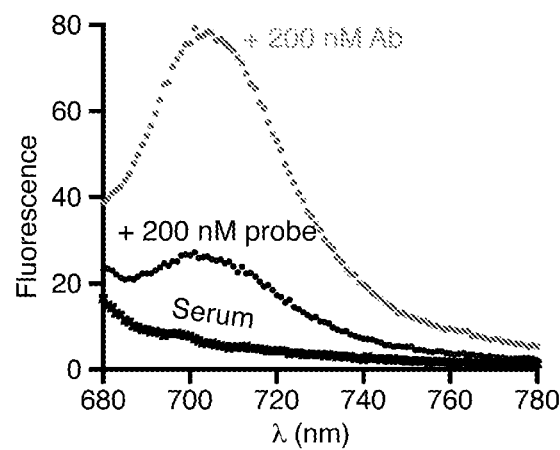
FIG. 7 (top) shows a graph of fluorescence vs. wavelength (nm) for probes for the detection of targets directly in blood serum, according to embodiments of the present disclosure.
Figure 7:
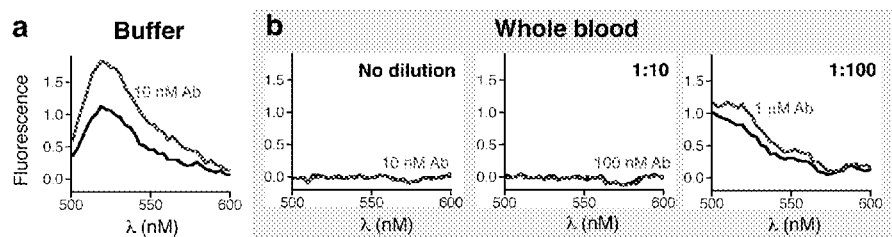

Experiments were also performed to test fluorescent probes for the detection of targets directly in blood serum. FIG. 7 (top) shows the detection of Dig-antibodies directly in blood serum at 37° C. using a modular oligonucleotide probe with the 3GC stem (see e.g., FIG. 5). The fluorescent signaling moieties used for FIG. 7 (top) were Alexa Fluor-680 for the fluorophore and BHQ-2 for the quencher (blood serum has a low fluorescence in the infrared). The fluorescent probe showed a lower detectable signal in whole blood as compared to blood serum (FIG. 7(b)). FIG. 7 (a) shows the detection of 10 nM Dig antibody using 10 nM of probe in: buffer (FIG. 7(a)); whole blood (FIG. 7(b), left); 1:10 whole blood (FIG. 7(b), middle); and 1:100 whole blood (FIG. 7(b), right). Fluorescence signal from the probe was not significantly detectable in whole blood or in a 1:10 whole blood sample due to high absorbance of the sample. Whole blood samples were diluted 100-fold or more to produce a detectable fluorescence signal (e.g., a final concentration of 10 nM of antibody after a 1:100 dilution corresponds to an antibody concentration of 1 µM in whole blood). For FIG. 7, panels a and b, the fluorescent signaling moieties used were FAM-6 for the fluorophore and BHQ-1 for the quencher.

Fluorescent Probes for DNA-Binding Protein Detection

A DNA-based probe that binds to TATA binding protein (TBP) was made. The probe included a DNA sequence that adopts both a "dark" double stem-loop structure and a "bright" fluorescent single stem-loop conformation, the latter of which includes a TBP recognition duplex (FIG. 11). The gain and affinity, and thus sensitivity, of the probes may depend on the thermodynamics of the conformational change between the double stem-loop structure and the single stem-loop structure. Probes were made that had various stabilities when in the unbound conformation (FIG. 11(b)). As predicted by the population-shift model of conformational change, probes with high equilibrium constants (e.g., >9.5, such that the probes are >90% in the binding competent state even in absence of their target) do not respond appreciably after addition of TBP (FIG. 11(c)). Probes with equilibrium constants near unity, in contrast, exhibit a detectable difference in fluorescence in the presence of target (about twice as intense as the fluorescence observed in the absence of saturating target) and still retain high target affinity ($K_D$=36±6 nM). Further decreases in the equilibrium constant produce greater fluorescence changes upon target binding, but, as predicted by the population shift model, affinity for the target is reduced. For example, according to the model, a switching equilibrium constant of 0.006 produces a dissociation constant of 1.1 μM. In certain embodiments, the switching equilibrium constant ranges from 1 to 0.1, depending on whether the probe is configured for achieving a low detection limit or for achieving a high signal gain (e.g., for applications such as in vivo imaging).

DNA-based switches for the quantitative detection of DNA binding proteins were tested. FIG. 11(a) shows DNA sequences recognized by transcription factors (recognition sequences 1007 and 1008) that can be engineered into structure-switching probes by stabilizing an alternative double stem-loop conformation (FIG. 11(a), left). By adding a quencher and fluorophore at locations that experienced the largest distance separation upon switching, binding of the transcription factor to its specific double stranded DNA recognition duplex shifts the equilibrium of the sensor towards the fluorescent binding state. A $K_S$ ranging from 1 to 0.1 produced a probe configured to populate its darker state in absence of target binding without over-stabilizing this nonbinding state, which results in decrease affinity of the probe as predicted by the population-shift model. Predicted $K_S$ were evaluated from the difference in energy predicted between both states using mfold while experimental $K_S$ were determined from the fluorescence signal of the probe in absence of target.

Figure 12:
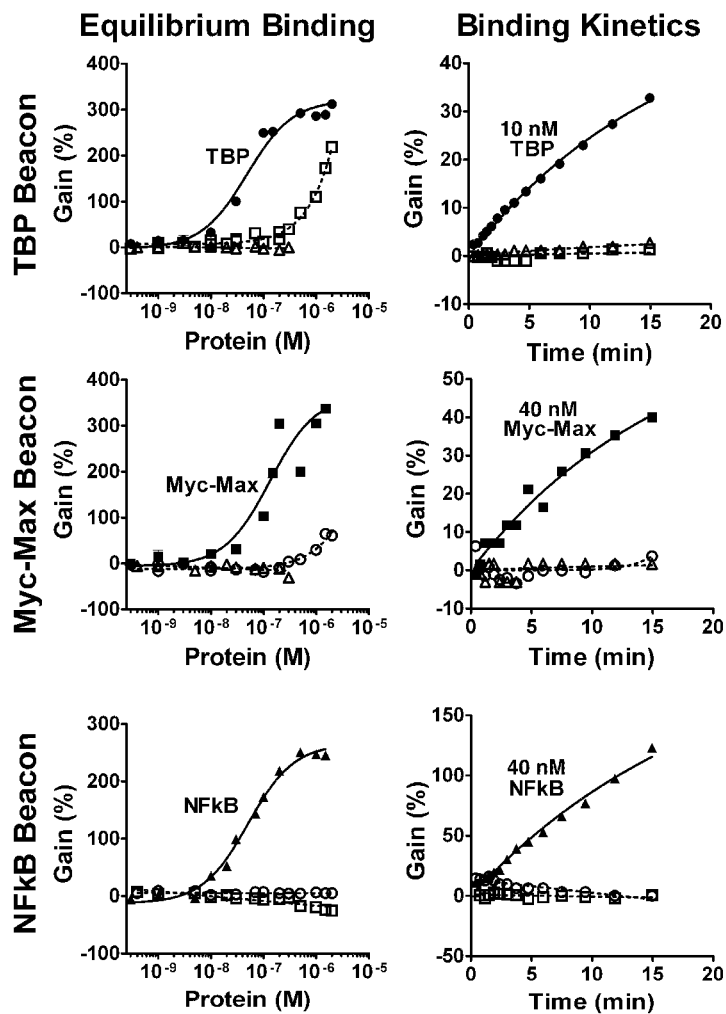
FIG. 12 shows graphs of fluorescence signal vs. target concentration for probes for detecting DNA binding proteins (e.g., TATA Binding Protein, Myc-Max, and NFkB), and their binding kinetics, according to embodiments of the present disclosure.

The TBP-detecting transcription factor probe shown in FIG. 12 had a switching equilibrium constant of 0.72 and produced a 300% increase in fluorescence in the presence of 100 nM concentrations of TBP, but no significant increase in fluorescence when in the presence of similar concentrations of other transcription factors such as Myc-Max and NF-KB. The TBP sensor was sensitive and rapid, able to detect 10 nM target in 5 minutes or less (FIG. 12, right).

Probes were also designed for the detection of the transcription factors Myc-Max and NFkB. Probe structures similar to those employed in the detection of TBP were used (FIG. 12, graphs in the middle and bottom rows). Using Myc-Max and NFkB-binding probes with switching thermodynamics similar to those used for TBP detection ($K_S$~0.3), resulted in signal gains, affinities, specificities, and kinetics similar to those achieved for the detection of TBP (FIG. 12, middle and bottom rows). Both the Myc-Max and NFkB probes showed signal gains of 300%, with $K_D$ of 53±12 nM and 134±41 nM, respectively. The probes were specific and exhibited only very low cross-reactivities (FIG. 12).

Figure 13:
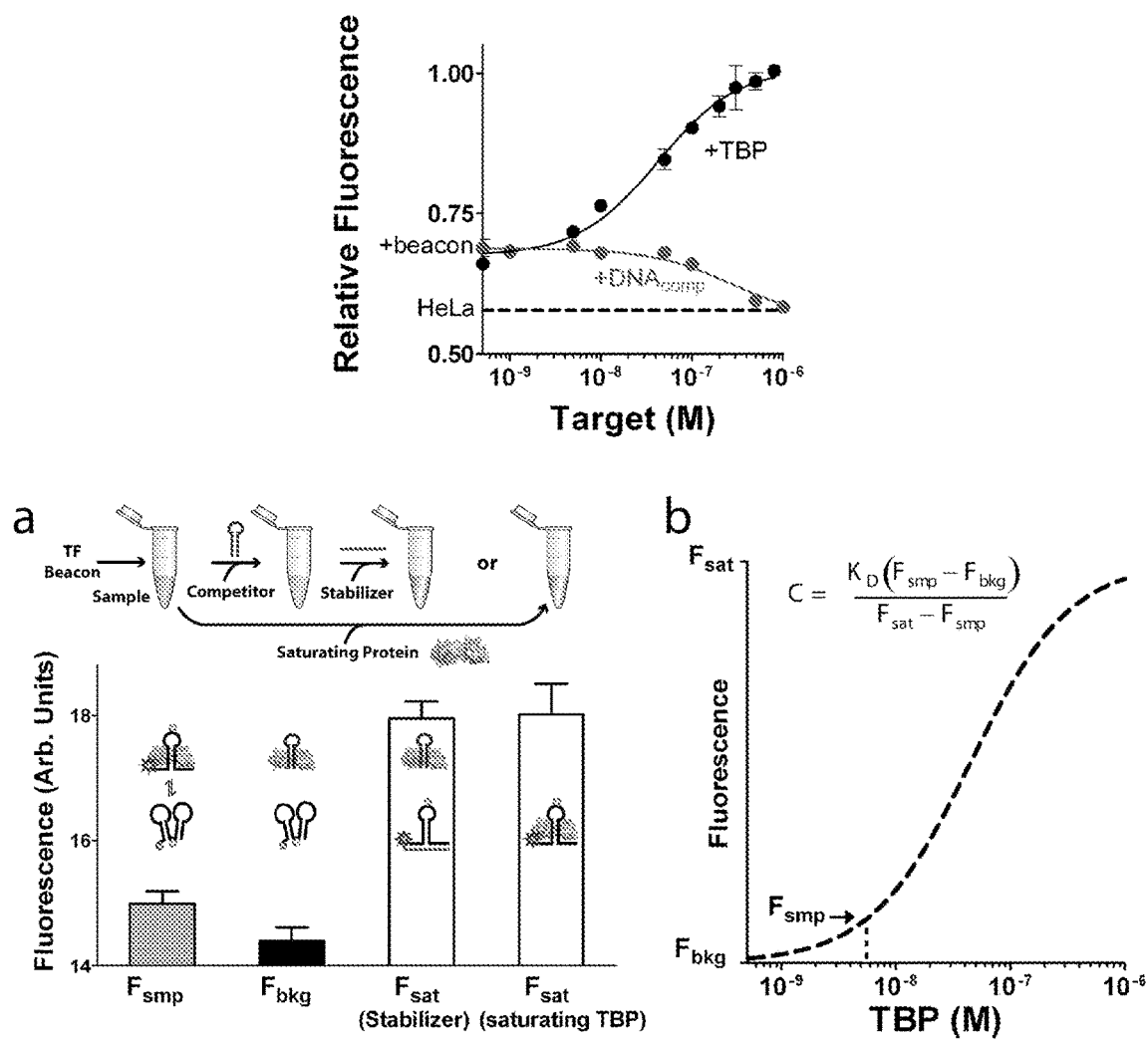
FIG. 13 (top) shows graphs of fluorescence signal vs. target concentration for probes for detecting DNA binding proteins directly in crude nuclear extracts (250 µg/mL of HeLa nuclear extracts) (+TBP), according to embodiments of the present disclosure.

The ability of the TBP transcription factor probe to function in HeLa nuclear cell extract was also tested (FIG. 13). A probe directed against TBP was titrated with its target protein against a background of 250 μg/mL crude HeLa nuclear extract (FIG. 13, top), producing a binding curve similar to that observed in buffer (see e.g., FIG. 12). The probe had an apparent dissociation constant that decreased from 45±3 nM in simple buffers to 36±6 nM in the extract. Without being limited to any particular theory, a possible explanation for this shift is that the true TBP concentration in this experiment was 9±7 nM higher than the concentration of exogenous TBP added at each point in the titration due to the presence of endogenous TBP. To characterize this further, an unlabeled, double-stranded TBP recognition oligonucleotide was introduced as a competitor ($DNA_{comp}$) and a dose-dependent decrease in fluorescence signal was observed, which was consistent with the presence of endogenous TBP (FIG. 13, top). The introduction of an unlabeled, double-stranded TBP recognition oligonucleotide as a competitor ($DNA_{comp}$) generated a loss of probe fluorescence signal consistent with the presence of endogenous TBP.

Transcription factor probes were tested to determine the detection and quantification of transcription factors in crude nuclear extracts (FIG. 13, bottom). Such quantification required measurement of the fluorescence of the probe-containing extract: (1) in equilibrium with the endogenous transcription factor population contained in the sample, $F_{smp}$; (2) in the background when no transcription factor was bound to the switch, $F_{bkg}$; and (3) when the switch was fully bound (e.g., saturated) with its transcription factor, $F_{sat}$. $F_{smp}$ was determined by adding 10 nM of the relevant transcription factor probe to the sample, and then measuring the fluorescence at the relevant emission maxima of the fluorophore after the system had substantially reached equilibrium. To determine $F_{bkg}$ and $F_{sat}$, the sample was spilt into two samples. $F_{bkg}$ was determined in one sample by adding a saturating concentration (>500 nM) of unlabeled, double-stranded recognition site that served as a competitor, liberating the free probe. $F_{sat}$ was determined via two strategies. First, by adding exogenous transcription factor to saturation (e.g., until all of the probe was in the emissive state). Alternatively, a single-stranded oligonucleotide complementary to the two tails of a probe in its binding competent state was added to drive the equilibrium of the probe into its fully emissive conformation (e.g., the target-bound state) (FIG. 13(a)). After $F_{bkg}$, $F_{sat}$ and $F_{smp}$ were determined, the concentration of the target protein, C, was determined by using the known dissociation constant of the probe, $K_D$, (42 nm) using the following formula:

$$C = \frac{K_D(F_{smp} - F_{bkg})}{F_{sat} - F_{smp}} \quad (1)$$

Using this approach, the endogenous TBP concentration in crude, 250 μg/mL HeLa nuclear extracts was 5.8±0.2 nM in 25% nuclear extract (250 μg/mL). This value was in reasonable agreement with both our estimate above (based on the shift in apparent dissociation constant (FIG. 13, top) and with the expected concentration (~3 nM) estimated from the number of copies of TBP per cell and the known number of cells in a given amount of nuclear extract (Borggrefe, T., et al., J. Biol. Chem. 2001, 276, pp. 47150).

Electrochemical Probes

Electrochemical Probes for Antibody Detection

Electroactive contaminants are generally rare (FIG. 8), which may facilitate electrochemical detection of targets in whole blood and other complex samples. For example, in the absence of target antibodies, the electrochemical readouts of probes modified with either Dig antigen or HIV peptide antigen increased only by 15-30% when transferred from buffer to whole blood (FIG. 8(e)). Electrochemical probes in which the fluorophore of the fluorescent probe was replaced with a thiol group for surface attachment, and the quencher of the fluorescent probe was replaced with a methylene blue redox reporter (FIG. 8(a)) were prepared. In the absence of target, the stem of the probe positioned the methylene blue electrochemical reporter in proximity to the electrode, promoting electron transfer and producing an increase in the faradaic current. Upon target binding, the methylene blue was positioned away from the electrode, decreasing electron transfer and generating a detectable current signal change (FIGS. 8(a) and 8(b)).

Electrochemical probes detected nanomolar concentrations of their targets directly in whole blood (FIGS. 8(b)-(d)). Blood doped with the relevant antibody targets (30 nM) produced a detectable decrease in the current signal from anti-Dig and anti-HIV antibody sensors (FIG. 8(b)). Blood doped with a mixture of 30 nM of the other sensor's target antibody and a 100-fold higher concentration of random, pooled human IgGs produced no significant change in the observed current (FIG. 8(b), dotted line). The anti-Dig and anti-HIV probes achieved 1 nM and 10 nM detection limits (e.g., 0.15 to 1.5 µg/ml), respectively (FIG. 8(c)), which was well below the serum concentrations typical of antibodies. These electrochemical probes achieved equilibration time constants of 5 min or less (FIG. 8(d)). The electrochemical probes did not measurably respond to non-targeted monoclonal or polyclonal antibodies at 30 nM even when mixed with a 3 µM mixture of random human antibodies (FIG. 8(d)). The titrations and kinetic traces shown in FIG. 8 represent the average of measurements conducted with at least four independently fabricated sensors, with error bars reflecting the average absolute deviation. Shown in FIG. 8(e) are square wave voltammograms for anti-Dig antibody and anti-HIV antibody probes in buffer and 80% whole blood. The graphs shown in FIG. 8(e) show how electrochemical probes were relatively insensitive to the presence of whole blood.

Figure 9:
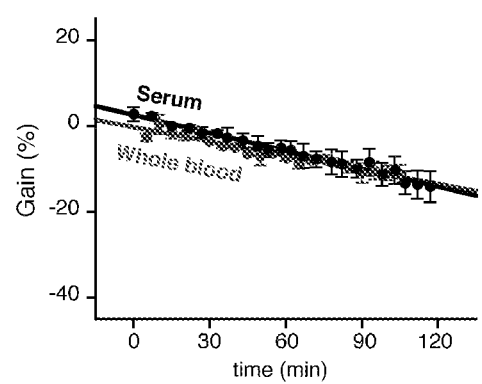
FIG. 9 shows a graph of non-specific signal degradation vs. time for an electrochemical probe in whole blood and blood serum, according to embodiments of the present disclosure.

Stability of the electrochemical probe (e.g., a unimolecular probe indirectly bound with Dig antigen) in whole blood and blood serum was tested (FIG. 9). The background of faradaic current of the sensor was reduced linearly by 6.6% and 8.4% per hour in whole blood and serum, respectively. The decrease in the background of faradaic current may have been due to the activity of DNA nucleases.

Stem-less probes with the target binding moieties at various locations (FIG. 10(a)) were also made and tested. The stem-less probes were labeled with an antigenic peptide epitope sequence and included an electrochemical reporter and an electrode as the signaling moieties. In the absence of target binding, the electrochemical reporter was able to be positioned proximal to the electrode, and thus transfer electrons with the electrode surface, thus generated a relatively large current (FIG. 10(b)). Specific target binding of, for example the anti-Flag antibody to the epitope recognition moieties, caused the flexible probe to switch to a substantially rigid, target-bound structure, thus producing a decrease in the signal (FIG. 10(c)) by about 80% with saturating antibody concentrations (FIG. 10(d)).

Electrochemical Probes for DNA-Binding Protein Detection

A DNA-based electrochemical probe for the detection of TATA binding protein (TBP) was also made. The probe included a DNA sequence that adopts both a "low-current-signal" double stem-loop structure and a "high-current-signal" single stem-loop conformation, the latter of which includes a TBP recognition duplex (FIG. 14). FIG. 14 (top) shows DNA sequences recognized by the TBP transcription factor (recognition sequences 1407 and 1408) that can be engineered into structure-switching probes by stabilizing an alternative double stem-loop conformation (FIG. 14 (top), left). The probe was also internally modified with an electrochemical reporter (e.g., methylene blue) and at one end with a thiol group for immobilization to a gold electrode surface. In the absence of the target DNA binding protein TBP the double stem-loop structure (FIG. 14 (top), left) positioned the methylene blue electrochemical reporter at a distance away from the electrode surface, thus decreasing the electron transfer rate and resulting in a low current signal. Upon TBP binding (FIG. 14 (top), right), the DNA probe was shifted towards the single stem-loop conformation and the electrochemical reporter was positioned in close proximity with the electrode surface. This, in turn, resulted in an increase in the current signal proportional to the concentration of the TBP target (FIG. 14(b). The TBP electrochemical sensor was sensitive and rapid, able to detect nanomolar concentrations of target in 5 minutes or less (FIG. 14(b)).

The ability of the TBP transcription factor electrochemical probe to function in HeLa nuclear cell extract was also tested (FIG. 14(b)). The probe directed against TBP was titrated with its target protein against a background of 250 µg/mL crude HeLa nuclear extract (FIG. 14(b), producing a binding curve similar to that observed in buffer (FIG. 14(b). This binding curve was slightly offset from the curve obtained in buffer. Without being limited to any particular theory, a possible explanation for this shift was that this was a contribution from the endogenous TBP present in cell extract. The TBP transcription factor electrochemical probe provided the convenient quantification of transcription factors in cell extract. The sensor's response in buffer, cell extract and, finally, extract to which a large excess of TBP had been added were measured. These measurements were used to calculate the concentration of TF in the sample, C, via the following relationship:

$$C = \frac{K_D(S_{samp} - S_{min})}{S_{max} - S_{samp}}$$

where $S_{min}$ is the minimum signal response, $S_{max}$ is the maximum signal response, and $S_{samp}$ is the signal response seen in the sample of interest. By performing a sequential addition and electrochemical measurement series in one sensor, measuring buffer, extract, and after further addition of 1 µM TBP, the endogenous TBP concentration was determined to be 4±2 nM, which was in close agreement with the results of prior studies.

Material and Methods

Fluorescent Probes:

HPLC purified DNAs modified with 5'-FAM, 3'-BHQ-1 and either Dig or DNP were purchased from IBA (Goettingen, Germany) and Biosearch Technologies (Novato, Calif.), respectively. All constructs possessed an additional adenine base after the FAM- and guanine nucleotide before the BHQ-1. Dig was inserted on a thymine modified nucleotide in the middle of the stem using a C8 linker (about 1 nm): 5'-FAM-ACTT(Dig)TGTTTTTTTGCGTTTTTTTTCA-T (Dig)AGG-BHQ-3' (SEQ ID NO:1). DNP was inserted between two nucleotides at a similar location using a C12 linker (about 1.5 nm): 5'-FAM-ACTT-DNP-TGTTTTTTTTTTTTTTTTTTCA-DNP-TAGG-3' (SEQ ID NO:2).

Modular Fluorescent Probes:

HPLC purified DNA containing a frame inversion and modified internally with thymine-labeled FAM and BHQ-1; purchased from IBA (Goettingen, Germany): 5'-TG-GATCGGCGTTTTATTTT(FAM)-CCTT-GTTTTTTTTTTTTTTTTTTCATGGT(BHQ)T-3'-3'TT-ATTTTGCGGCTAGGT-5' (SEQ ID NO:3). HPLC purified antigen-modified 17-base DNA sequences were obtained from IBA (Goettingen, Germany) (Dig-DNA): T(Dig)AATAAAACGCCGATCCA (SEQ ID NO:4); and Bio-synthesis (Lewisville, USA) (peptide-linker-DNA): ELLELD-KWASLWNC-(SMCC-NH-(CH2)$_6$PO$_3$)-AATAAAAC-GCCGATCCA (SEQ ID NOs:5 and 6) (HIV-1 gp41 epitope21 with a 4 amino acids linker -SMCC).

Fluorescent DNA Binding Protein Probes:

HPLC purified DNAs modified with 5'-FAM, and internal BHQ-1 inserted on a thymine residue were purchased from IBA (Goettingen, Germany) and Biosearch Technologies (Novato, Calif.). DNA binding proteins TBP and Myc-Max were recombinantly expressed, purified, and characterized as previously described (Bonham 2009; Martinez 2004). Recombinant NFkB (p50 homo-dimer) was purchased from ActiveMotif (Carlsbad, Calif.) and used as purchased. HeLa cell nuclear extract was purchased from Santa Cruz Biotechnologies (Santa Cruz, Calif.) and used as purchased.

Electrochemical Probes for Antibody Detection:

HPLC purified DNA with a frame inversion, and modified with internal C6-thiol and methylene blue (MB) was purchased from Bio search Technologies (Novato, Calif.): 5'-TGGATCGGCGTTTTATTTTT(C6-Thiol)CCTTGT-TTTTTTTTTTTTTTTT-CATGG-T(MB)TT-3'-3'-TT-ATTTTGCGGC-TAGGT-5' (SEQ ID NO:7).

Antibodies were purchase from Roche Diagnostic Corporation (Mannheim, Germany) (Sheep polyclonal anti-digoxigenin and its Fab fragments), Sigma-Aldrich (St. Louis, Mo.) (Mouse Monoclonal Anti-DNP), and Polymun Scientific (Vienna, Austria) (antibody 2F5 specific for gp41). Heparinized whole blood (bovine calf) was purchase from Innovative Research (Michigan, USA).

Electrochemical Probes for DNA-Binding Protein Detection:

HPLC purified DNA modified with terminal C6-thiol and internal methylene blue (MB) was purchased from Biosearch Technologies (Novato, Calif.): 5'-(C6-Thiol)GAATAGGTTCC-TATAAAA-GGTTGG-TTTTATA-AAC-CTAT (MB) CCTATTC-3' (SEQ ID NO:8).

All fluorescent experiments were conducted at pH 7 in 50 mM sodium phosphate buffer, 150 mM NaCl, 10 mM MgCl$_2$ at 20° C., unless otherwise indicated. This buffer was supplemented with 5 mM MgCl$_2$ for all experiments with TBP. Equilibrium fluorescence measurements were obtained using a Cary Eclipse Fluorimeter with excitation at 480 (±5) nm and acquisition at 517 (±5) nm Fluorescence spectra were obtained using 10 nM solutions of probe. Binding curves were obtained using 4 nM of probes (and 8 nM of antigen-modified 17-base DNA for the modular probes) by sequentially increasing the antibody concentration via the addition of small volumes of solutions with increasing concentrations of target. Dissociation constants were obtained using classic two-state dose-response curves. The apparently bi-linear (sharper) response obtained for the anti-Dig antibody probe, which, if fit to a two-state binding equation, produced an apparent dissociation constant of 2 nM (FIGS. 2 and 3), thus suggesting that the true dissociation constant of this system was lower than the 4 nM probe concentration employed. Kinetic fluorescence data were obtained using an SM-18 Applied-Photophysics stopped-flow instrument by excitation at 480 (±10) nm and monitoring the total fluorescence above 495 nM using a cut-off filter.

Electrochemical measurements in buffer (1M NaCl, 0.05% Tween, 0.1% BSA), in nuclear extract (250 ug/mL HeLa nuclear cell extract), or in whole blood (similarly buffered with a 5× stock solution) were performed at room temperature using a CHI630C potentiostat with a CHI684 Multiplexer (CH Instruments, Austin, Tex.) and a standard three-electrode cell containing a platinum counter electrode (BAS) and a Ag/AgCl (3M NaCl) reference electrode (BAS). Electrodes were fabricated as described in the literature using a low probe density of $2 \times 10^{11}$ molecules/cm$^2$ to insure that antibodies did not bind antigens located on two different probes. The electrode-bound modular DNA-probes were modified with their respective antigens by incubating the electrodes 30 minutes in a solution containing 100 nM of antigen-modified 17-base DNA. Square wave voltammograms were collected at 60 Hz from −0.05 to −0.45 in increments of 0.001 V vs. Ag/AgCl with an amplitude of 50 mV. Peak currents were fit using the manual fit mode in the CH Instruments software. With the exception of kinetic measurements, all measurements were obtained after 20 min incubations following an initial 20 minutes incubation of the probe in buffered whole blood. Gains represent difference in peak currents obtained before and after target addition divided by initial peak current.

The preceding merely illustrates the principles of the disclosure. All statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, e.g., any elements developed that perform the same function, regardless of structure. The scope of the present disclosure, therefore, is not intended to be limited to the exemplary embodiments shown and described herein. Rather, the scope and spirit of present disclosure is embodied by the appended claims.

That which is claimed is:

1. A system for detecting one or more targets in a sample, the system comprising:
   (a) a first oligonucleotide configured to produce a detectable change in signal when bound by a target in a sample, wherein the first oligonucleotide comprises:
   a first hybridization sequences;
   a second hybridization sequence complementary to the first hybridization sequence such that a duplex is formed in the absence of the target;
   a third hybridization sequence;
   a fourth hybridization sequence;
   a first signaling moiety attached to the first oligonucleotide, wherein the first signaling moiety comprises a fluorophore, a quencher, a nanoparticle, an electrochemical reporter, or an electrode; and
   a second signaling moiety attached to the first oligonucleotide, wherein the second signaling moiety comprises a fluorophore, a quencher, a nanoparticle, an electrochemical reporter, or an electrode;
   (b) a second oligonucleotide attached to a first target binding moiety and comprising a fifth hybridization sequence complementary to the third hybridization sequence, wherein the first target binding moiety is configured to specifically bind the target in the sample and comprises a protein, a polypeptide, a carbohydrate, a nucleic acid, a lipid, or a small molecule; and
   (c) a third oligonucleotide attached to a second target binding moiety and comprising a sixth hybridization sequence complementary to the fourth hybridization sequence such that the second target binding moiety is positioned adjacent to the first target binding moiety in the absence of the target, wherein the second target binding moiety is configured to specifically bind the target in the sample and comprises a protein, a polypeptide, a carbohydrate, a nucleic acid, a lipid, or a small molecule,
   wherein in the presence of binding of the target to both the first target binding moiety and the second target binding moiety, formation of the duplex is inhibited such that the position of the first signaling moiety is changed relative to the second signaling moiety such that the first oligonucleotide produces a detectable change in signal.

2. The system of claim 1, wherein the first oligonucleotide comprises a stem-loop structure in the absence of the target binding to the first target binding moiety and the second target binding moiety.

3. The system of claim 1, wherein the third hybridization sequence and the fourth hybridization sequence are substantially the same, the fifth hybridization sequence and the sixth hybridization sequence are substantially the same, and wherein the first oligonucleotide comprises a frame inversion between the third hybridization sequence and the fourth hybridization sequence.

4. The system of claim 3, wherein the frame inversion is a 3' to 3' or a 5' to 5' frame inversion.

5. The system of claim 1, wherein the first target binding moiety and the second target binding moiety comprise antigens, and wherein the target comprises an antibody specific for the antigens.

6. The system of claim 1, wherein the first target binding moiety and the second target binding moiety comprise polypeptides that specifically bind to a macromolecule, and wherein the target comprises the macromolecule.

7. The system of claim 1, wherein the first target binding moiety and the second target binding moiety comprise aptamers that specifically bind to a macromolecule, and wherein the target comprises the macromolecule.

8. The system of claim 1, wherein the first target binding moiety and the second target binding moiety comprise DNA or RNA sequences that specifically bind to a macromolecule, and wherein the target comprises the macromolecule.

9. The system of claim 1, wherein the sample comprises the system and a target and the target is present in a concentration ranging from 1 pM to 100 nM.

10. The system of claim 1, wherein the first signaling moiety comprises a fluorophore and the second signaling moiety comprises a quencher.

11. The system of claim 1, wherein the first signaling moiety comprises a first fluorophore and the second signaling moiety comprises a second fluorophore.

12. The system of claim 1, wherein the first signaling moiety comprises a nanoparticle and the second signaling moiety comprises a quencher.

13. The system of claim 1, wherein the first signaling moiety comprises a first nanoparticle and the second signaling moiety comprises a second nanoparticle.

14. The system of claim 1, wherein the first signaling moiety comprises an electrochemical reporter and the second signaling moiety comprises an electrode.

15. The system of claim 14, wherein the first oligonucleotide is immobilized on a surface of the electrode.

16. The system of claim 15, wherein the system comprises an array of first oligonucleotides.

17. The system of claim 1, wherein the first signaling moiety comprises a macromolecule having a catalytic activity and the second signaling moiety comprises an inhibitor or an activator of the catalytic activity.

18. A method of detecting a target in a sample, the method comprising:
contacting the system of claim 1 with the sample, whereby the target selectively binds to both the first target binding sequence and the second target binding sequence to form a hybrid; and
detecting the presence or absence of the hybrid.

19. The method of claim 18, wherein the sample comprises a complex sample.

20. The method of claim 19, wherein the sample comprises whole blood.

21. A method of detecting a second target in a sample, the method comprising:
contacting the system of claim 1 with the sample, whereby the target selectively binds to both the first target binding sequence and the second target binding sequence to form a hybrid;
contacting the hybrid with a second target, whereby the second target selectively binds the target and inhibits formation of the hybrid; and
detecting the presence or absence of the hybrid.

22. The system of claim 1, wherein the system is configured to detect the target at a concentration ranging from 1 pM to 100 nM in the sample.

23. The system of claim 1, further comprising a detector configured to detect the detectable change in signal.

* * * * *

UNITED STATES PATENT AND TRADEMARK OFFICE
CERTIFICATE OF CORRECTION

PATENT NO. : 9,828,628 B2  
APPLICATION NO. : 13/988487  
DATED : November 28, 2017  
INVENTOR(S) : Alexis Vallée-Bélisle et al.

Page 1 of 1

It is certified that error appears in the above-identified patent and that said Letters Patent is hereby corrected as shown below:

On the Title Page

Item (75), Line 1, "Alexis Vallé- Bélisle" should read -- Alexis Vallée-Bélisle --

Signed and Sealed this  
Seventeenth Day of April, 2018

Andrei Iancu  
*Director of the United States Patent and Trademark Office*